(12) United States Patent
Baguisi et al.

(10) Patent No.: US 9,359,325 B2
(45) Date of Patent: Jun. 7, 2016

(54) LIPOYL COMPOUNDS AND METHODS FOR TREATING ISCHEMIC INJURY

(71) Applicant: Ischemix LLC, Maynard, MA (US)

(72) Inventors: Alexander B. Baguisi, Grafton, MA (US); Reinier Beeuwkes, Concord, MA (US); Ralph Casale, Westford, MA (US); Steven A. Kates, Needham, MA (US); Alan S. Lader, Stoughton, MA (US)

(73) Assignee: Ischemix LLC, Maynard, MA (US)

( * ) Notice: Subject to any disclaimer, the term of this patent is extended or adjusted under 35 U.S.C. 154(b) by 0 days.

(21) Appl. No.: 14/456,646

(22) Filed: Aug. 11, 2014

(65) Prior Publication Data

US 2015/0065564 A1  Mar. 5, 2015

Related U.S. Application Data

(63) Continuation of application No. 13/885,289, filed as application No. PCT/US2011/060259 on Nov. 10, 2011, now Pat. No. 8,815,937.

(60) Provisional application No. 61/415,240, filed on Nov. 18, 2010, provisional application No. 61/415,241, filed on Nov. 18, 2010, provisional application No. 61/478,310, filed on Apr. 22, 2011, provisional application No. 61/500,974, filed on Jun. 24, 2011.

(51) Int. Cl.

| A61K 31/385 | (2006.01) |
|---|---|
| C07D 339/04 | (2006.01) |
| A61K 47/48 | (2006.01) |
| C07F 9/6553 | (2006.01) |
| C07K 5/062 | (2006.01) |
| C07K 5/065 | (2006.01) |
| C07K 5/072 | (2006.01) |

(52) U.S. Cl.
CPC ........ C07D 339/04 (2013.01); A61K 47/48246 (2013.01); C07F 9/655345 (2013.01); C07K 5/06026 (2013.01); C07K 5/06078 (2013.01); C07K 5/06104 (2013.01); C07K 5/06113 (2013.01)

(58) Field of Classification Search
CPC ............................ A61K 31/385; C07D 339/04
USPC ............................... 549/29, 39; 514/430, 440
See application file for complete search history.

(56) References Cited

U.S. PATENT DOCUMENTS

| 3,875,207 | A | 4/1975 | Iselin et al. |
|---|---|---|---|
| 5,288,706 | A | 2/1994 | Yamanouchi et al. |
| 5,318,987 | A | 6/1994 | Wieithmann et al. |
| 6,013,663 | A | 1/2000 | Fujita et al. |
| 6,127,339 | A | 10/2000 | Hatanaka et al. |
| 6,271,254 | B1 | 8/2001 | Ulrich et al. |
| 6,544,718 | B2 | 4/2003 | Goto |
| 6,890,896 | B1 | 5/2005 | Shashoua |
| 7,524,819 | B2 | 4/2009 | Shashoua |
| 7,928,067 | B2* | 4/2011 | Baguisi et al. ............... 514/16.4 |
| 8,410,162 | B2 | 4/2013 | Garner et al. |
| 8,772,249 | B2 | 7/2014 | Baguisi et al. |
| 8,772,250 | B2 | 7/2014 | Baguisi et al. |
| 8,815,937 | B2 | 8/2014 | Baguisi et al. |
| 2002/0035243 | A1 | 3/2002 | Imfeld et al. |
| 2002/0048798 | A1 | 4/2002 | Avery et al. |
| 2004/0204340 | A1 | 10/2004 | Hamilton et al. |
| 2005/0153291 | A1 | 7/2005 | Harwich et al. |
| 2006/0019901 | A1 | 1/2006 | Shashoua |
| 2007/0287195 | A1 | 12/2007 | Suda |
| 2009/0082281 | A1 | 3/2009 | Shashoua |
| 2009/0306190 | A1 | 12/2009 | Stenzel-Poore et al. |
| 2010/0292313 | A1 | 11/2010 | Baguisi et al. |
| 2011/0160294 | A1 | 6/2011 | Baguisi et al. |
| 2012/0135932 | A1 | 5/2012 | Baguisi et al. |
| 2013/0237483 | A1 | 9/2013 | Baguisi et al. |
| 2014/0274917 | A1 | 9/2014 | Baguisi et al. |
| 2015/0329519 | A1 | 11/2015 | Kates et al. |

FOREIGN PATENT DOCUMENTS

| CA | 2582027 | 9/2007 |
|---|---|---|
| EP | 0 063 879 | 11/1989 |
| EP | 0424282 A1 | 4/1991 |
| EP | 0 869 126 | 7/2002 |
| EP | 1371640 A1 | 12/2003 |
| EP | 1 454 627 | 9/2004 |
| JP | 9-90542 | 4/1997 |

(Continued)

OTHER PUBLICATIONS

Saito et al (2006): STN International HCAPLUS database, (Columbus, Ohio), Accession No. 2006:74266.*

Bala, M., et al., "Novel Peptidominics as Angiotensin-Converting Enzyme Inhibitors: A Combinatorial Approach," Bioorganic and Medicinal Chemistry, 10(11):3685-3691 (2002).

Bilska, A., et al., "Lipoic Acid—The Drug of the Future?", Pharmacological Reports, 57(5): 570-577 (Jan. 2005).

International Search Report and Written Opinion for PCT/US2011/060259, "Lipoyl Compounds and Methods for Treating Ischemic Injury", mailed Jan. 27, 2012, 5 pages.

Notification Concerning Transmittal of International Preliminary Report on Patentability and Written Opinion for 4 PCT/US2011/060259, "Lipoyl Compounds and Methods for Treating Ischemic Injury", mailed May 30, 2013, 9 pages.

(Continued)

Primary Examiner — Golam M M Shameem
(74) Attorney, Agent, or Firm — Hamilton, Brook, Smith & Reynolds, P.C.

(57) ABSTRACT

The present invention relates, in various embodiments, to a compound represented by Structural Formula (I), pharmaceutically acceptable salts or prodrugs thereof, and compositions comprising said compounds, or pharmaceutically acceptable salts or prodrugs thereof. Methods of using compounds of Structural Formulas (I) and (Ia) or compositions comprising compounds of Structural Formulas (I) and (Ia), or pharmaceutically acceptable salts or prodrugs thereof, to treat ischemia or ischemia-reperfusion injury are also disclosed.

10 Claims, No Drawings

(56) References Cited

FOREIGN PATENT DOCUMENTS

| JP | 11-7099 | 1/1999 |
|---|---|---|
| JP | 2000 169371 | 6/2000 |
| JP | 2003-048833 | 2/2003 |
| JP | 2003-286168 | 10/2003 |
| JP | 2004-51624 | 2/2004 |
| JP | 2006-22066 | 1/2006 |
| JP | 2007 070303 A | 3/2007 |
| NZ | 596364 | 10/2013 |
| WO | WO 93/22320 | 11/1993 |
| WO | WO 97/18235 | 5/1997 |
| WO | WO 99/45922 | 9/1999 |
| WO | WO 01/09118 | 2/2001 |
| WO | WO 01/36454 | 5/2001 |
| WO | WO 02/096360 | 12/2002 |
| WO | WO 03/355853 | 7/2003 |
| WO | WO 03/070714 | 8/2003 |
| WO | WO 03/072052 | 9/2003 |
| WO | WO 2004/004632 | 1/2004 |
| WO | WO 2005/063732 | 7/2005 |
| WO | WO 2006/101909 | 9/2006 |
| WO | WO 2006/117995 | 11/2006 |
| WO | WO 2007/027559 | 3/2007 |
| WO | WO 2010/052310 A1 | 5/2010 |
| WO | WO 2006/101910 | 9/2010 |
| WO | WO 2010132657 | 11/2010 |
| WO | WO 2010147957 | 12/2010 |
| WO | WO 2011080725 | 7/2011 |
| WO | WO 2012067947 | 5/2012 |

OTHER PUBLICATIONS

Panigrahi, M., et al., "[alpha]-Lipoic Acid Protects Against Reperfusion Injury Following Cerebral Ischernia in Rats," Brain Research 717(1-2): 184-188 (1996).
1995-6 Sigma Peptides and Amino Acids Catalog, pp. 143-144.
Adger, B., et al., "The Synthesis of (R)-(+)-Lipoic Acid Using a Monooxygenase-Catalysed Biotransformation as the Key Step," Bioorganic and Mechanical Chemistry, 5(2): 253-261 (1997).
Anderson, MD, Cancer Center News Release Dated Feb. 25, 2010, "New Strategy Develops Two Prototype Drugs Against Cancer, Retinal Diseases," Retrieved from internet on Dec. 1, 2010: http://www.mdanderson.org/newsroom/news-releases/2010/new-strategy-develops-two-pr[insert 3 periods], 4 pages.
Bartzatt, R.L., "Utilizing a D-Amino Acid as a Drug Carrier for Antineoplastic Nitrogen Mustard Groups," Drug Delivery, 12(3): 141-147 (2005), abstract only.
Bastin, R.J., et al., "Salt Selection and Optimisation Procedures for Pharmaceutical New Chemical Entities," Organic Process Res. And Dev., 427-435 (2000).
Berg, T., et al. Biochemistry Fifth Edition, pp. 43, 467 and 468 (2001).
Bessalle, R. et al., "All-D-magainin: Chirality, Antimicrobial Activity and Proteolytic Resistance," FEBS Lett., 274(1, 2): 151-155 (Nov. 1990).
Biewenga, G., et al., "The Pharmacology of the Antioxidant Lipoic Acid," Gen. Pharmac., 29(3): 315-331 (1997).
Branden, C. and J. Tooze, Introduction to Protein Structure 2nd. Ed. pp. 4-5 (1999).
Bunjes, N., et al., "Thiopeptide-Supported Lipid Layers on Solid Substrates," Langmuir, 13:6188-6194 (1997).
CAPLUS Accession No. 2006-1007709, CAS abstract for Kates WO 2006101909, published 2006.
CAPLUS Accession No. 2008: 1371872, published 2008.
CAS display of compounds in WO 2006/101909, published Sep. 28, 2006 and entitled "Combination Therapy for Treating and Preventing Diseases."
Chemical Abstract Service Job Listing for Scientific Information Analysis, Retrieved from internet on Oct. 20, 2010: https://jobs.cas.org/epostings/submit.cfm?fuseaction=app.jobinfo[insert ampersand]jobid=205158[insert ampersand]compa.
Chemical Abstract Service, Job Listing for Part-Time Organic Chemistry, Retrieved from internet on Oct. 20, 2010: https://jobs.cas.org/epostings/submit.cfm?fuseaction=app.jobinfo [insert ampersand]id=23[insert ampersand]jobid=205101.
Clever Approach May Provide New Clues to Drug Design, Retrieved from Internet on Dec. 9, 2010: http://www.wi.mit.edu/scripts/pfl.php?p=http:/www.wi.mit.edu/news/archives/1996/pk_0[insert 3 periods], 2 pages.
Creighton, T.E., Structure and Molecular Properties 2nd. Ed. p. 2 (1984).
Development and Uses of Alitame: A Novel Dipeptide Amide Sweetener, Glowaky, R.C. et al., Abstract only, Retrieved from Internet on Nov. 19, 2010: http://pubs.acs.org/doi/abs/10.1021/bk-1991-0450.ch005.
Fields, G.B. and R.L. Noble, "Solid Phase Peptide Synthesis Utilizing 9-Fluorenylmethosycarbonyl Amino Acids," Int. J. Peptide Protein Res. 35: 161-214 (1990).
Hagen, T.M., et al., "(R)-alpha-Lipoic Acid Reverses the Age-Assosciated Increase in Susceptibility of Hepatocytes to tert-Butylhydroperoxide Both In Vitro and In Vivo," Antioxidants and Redox Signaling, 2(3): 473-486 (****).
Hardesty, J.O., et al., "Enzymatic Proteolysis of a Surface-Bound α-Helical Polypeptide," Langmuir 24: 13944-13956 (2008).
Holmquist, L., et al., "Lipoic Acid as a Novel Treatment for Alzheimer's Disease and Related Dementias," Pharmacology and Therapeutics, 113: 154-164 (2007).
Jia, L., et al., "Protective Effect of Lipoic Acid Against Acrolein-Induced Cytotoxicity in IMR-90 Human Fibroblasts," J. Nutr. Sci. Vitaminol., 55: 126-130 (2009).
Khoronenkova, S.V. and Tishkov, V.I, "D-Amino Oxidase: Physiological Role and Applications," Biochemistry, 73(13):1511-1518 (2008).
Kilic, F., et al., "Modelling Cortical Cataractogenesis XX. In Vitro Effect of Alpha-Lipoic Acid on Glutathione Concentrations in Lens in Model Diabetic Cataractogenesis," Biochemistry and Molecular Biology International, 46(3): 585-595 (Oct. 1998).
Metabolism of Nitrogen-Containing Compounds. Biochemistry, Zubay, p. 592, Table 24.2 (1998).
Nomenclature Policy: Abbreviated Designations of Amino Acids, Am. J. Clin. Nutr., 47, 589 (1988).
Nomenclature Policy: Generic Descriptors and Trivial Names for Vitamins and Related Compounds, Am. J. Clin. Nutr. 47: 581-588 (1988).
NovaBiochem. Catalog and Peptide Synthesis Handbook pp. x, xi, 1, 2, 18, 19 (1999).
Packer, L., et al., "Molecular Aspects of Lipoic Acid in the Prevention of Diabetes Complications," Nutrition, 17: 888-895 (2001).
Pick, U., et al., "Glutathione Reductase and Lipoamide Dehydrogenase Have Opposite Stereospecficities for α-Lipoic Acid Enantiomers," Biochem. and Biophys. Res. Comm. 206(2): 724-730 (Jan. 1995).
Sehirli, O., et al., "α-Lipoic Acid Protects Against Renal Ischaemia-Reperfusion Injury in Rats," Clin. Exp. Pharmacol. Phys., 35: 249-255 (2008).
Sela, M. and Zisman, E., "Different Roles of D-Amino Acids in Immune Phenomena," The FASEB Journal, 11: 449 (1997).
Smith, J.R., et al., "Differential Activity of Lipoic Acid Enantiomers in Cell Culture," Journal of Herbal Pharmacotherapy, 5(3): 43-54 (2005).
STN Tokyo, International, L-Alanine, N-[5-(3R)-1,2-dithiolan-3-yl-1-oxopentyl]-L-beta-glutamyl-, file Registry [online], uploaded on Oct. 18, 2006, [searched on Jun. 6, 2013], CAS Registry No. 910627-26-8.
Van Der Meijden, M.W. et al., "Attrition-Enhanced Deracemization in the Synthesis of Clopidogrel—A Practical Application of a New Discovery," Organic Process Research and Development 13: 1195-1198 (2009).
Yu, G.L., et al., "Montelukast, a Cysteinyl Leukotriene Receptor-1 Antagonist, Dose- and Time-Dependently Protects against Focal Cerebral Ischemia in Mice," Pharmacology 73:31-40 (2005).
Wolz, P. and J. Krieglstein, "Neuroprotective Effects of α-Lipoic Acid and Its Enantiomers Demonstrated in Rodent Models of Focal Cerebral Ischemia," Neuropharmacology, 35(3): 369-375 (1996).

(56) References Cited

OTHER PUBLICATIONS

Zimmer, G., et al., "Dose/Response Curves of Lipoic Acid R- and S-Forms in the Working Rat Heart During Reoxygenation: Superiority of the R-Enantiomer of Enhancement of Aortic Flow," *J. Mol. Cell. Cardiol.* 27: 1895-1903 (1995).
Zimmer, R., et al., "Enantioselective Synthesis of (S)- and (R)-6-Hydroxy-8-nonenecarboxylates by Asymmetric Catalysis: A Formal Synthesis of (R)-α-Lipoic Acid and Its (S)-Antipode," *Tetrahedron: Asymmetry*, 11:879-887 (2000).
International Preliminary Report on Patentability for PCT/US2010/034701, entitled "Compositions and Methods for Treating Ischemia and Ischemia-Reperfusion Injury;" Date of Issuance: Nov. 15, 2011.
International Search Report and Written Opinion for PCT/US2010/034701, entitled "Compositions and Methods for Treating Ischemia and Ischemia-Reperfusion Injury;" Date Mailed: Jul. 15, 2010.
International Search Report and Written Opinion for PCT/US2011/060259, entitled "Lipoyl Compounds and Their Use for Treating Ischemic Injury;" Date of Mailing: Jan. 27, 2012.
Hagen, T.M., et al., "(R)-alpha-Lipoic Acid Reverses the Age-Associated Increase in Susceptibility of Hepatocytes to tert-Butylhydroperoxide Both In Vitro and In Vivo," Antioxidants and Redox Signaling, 2(3): 473-486 (2000).
Sato, et al., STN International HCAPLUS database, Columbus, Ohio, Accession No. 2006:74266.
Office Action dated Nov. 4, 2013 for U.S. Appl. No. 13/041,001, entitled "Compositions and Methods for Treating Ischemia and Ischemia-Reperfusion Injury."
Office Action dated Nov. 1, 2013 for U.S. Appl. No. 13/319,839, entitled "Compositions and Methods for Treating Ischemia and Ischemia-Reperfusion Injury."
Notice of Allowance dated Mar. 10, 2014 for U.S. Appl. No. 13/319,839, entitled "Compositions and Methods for Treating Ischemia and Ischemia-Reperfusion Injury."
Notice of Allowance dated Feb. 25, 2014 for U.S. Appl. No. 13/041,001, entitled "Compositions and Methods for Treating Ischemia and Ischemia-Reperfusion Injury."
Notice of Allowance, U.S. Appl. No. 13/885,289, dated Jul. 14, 2014.
Office Action, U.S. Appl. No. 13/885,289, dated Feb. 28, 2014.
Office Action, U.S. Appl. No. 13/885,289, dated Oct. 17, 2013.
NZ 610378, First Exam Report, "Lipoyl Compounds and Their Use for Treating Ischemic Injury," dated Feb. 17, 2014.
CN 2011800652141, First Office Action, "Lipoyl Compounds and Their Use for Treating Ischemic Injury," dated Oct. 8, 2014.
Office Action for U.S. Appl. No. 12/466,170, "Compositions and Methods for Treating Ischemia and Ischemia-Reperfusion Injury", Dated: Jul. 22, 2009.
Kates, S., et al., "Lipoic acid analogs with enhanced pharmacological activity," Bioorganic & Medicinal Chemistry 22(1):505-512 (2014).
International Search Report and Written Opinion, mailed Jul. 31, 2014 for PCT/US2014/000090, "Compositions and Methods for Treating Ischemia and Ischemia-Reperfusion Injury".
Office Action, dated Apr. 21, 2015, for U.S. Appl. No. 14/283,844, "Compositions and Methods for Treating Ischemia and Ischemia-Reperfusion Injury".
Nomenclature Policy: Abbreviated Designations of Amino Acids, Am. J. Clin. Nutr., 47, 581-588 (1988).
Written Opinion for SG Application No. 2013036546, "Lipoyl Compounds and Their Use for Treating Ischemic Injury", dated Aug. 5, 2014.
Second Written Opinion for SG Application No. 2013036546, "Lipoyl Compounds and Their Use for Treating Ischemic Injury", dated Jun. 23, 2015.

* cited by examiner

LIPOYL COMPOUNDS AND METHODS FOR TREATING ISCHEMIC INJURY

RELATED APPLICATIONS

This application is a continuation of U.S. application Ser. No. 13/885,289, now U.S. Pat. No. 8,815,937, issued Aug. 26, 2014, which is the U.S. National Stage Application of International Application No. PCT/US2011/060259 filed on Nov. 10, 2011, published in English, which claims the benefit of U.S. Provisional Application No. 61/415,240, filed on Nov. 18, 2010; U.S. Provisional Application No. 61/415,241, filed on Nov. 18, 2010; U.S. Provisional Application No. 61/478,310, filed on Apr. 22, 2011; and U.S. Provisional Application No. 61/500,974, filed on Jun. 24, 2011. The entire contents of the above applications are incorporated herein by reference.

BACKGROUND OF THE INVENTION

Coronary heart disease is a leading cause of death and injury worldwide. Following an acute myocardial infarction (MI), early restoration of blood flow is the most effective strategy for reducing the size of the MI. Paradoxically, restoring blood flow to the area of the heart that is affected by the diminished flow can, in itself, be harmful. This is called reperfusion injury and can, by some estimates, be responsible for up to 50% of the final size of the MI (Yellon D. M., Hausenloy D. J., Myocardial reperfusion injury. *New England Journal of Medicine* 2007, 357:1121). The final size of the MI ultimately determines how well the heart can function after a heart attack.

Myocardial ischemia-reperfusion injury is defined as myocardial injury caused by the ischemic injury combined with injury caused by the restoration of coronary blood flow after an ischemic episode. Ischemia-reperfusion injury is mediated by an influx of calcium ions and depletion of oxygen during an ischemic event, followed by reoxygenation and generation of reactive oxygen species during reperfusion (Piper, H. M., Abdallah, C., Schafer, C., The first minutes of reperfusion: a window of opportunity for cardioprotection. *Annals of Thoracic Surgery* 2003, 75:644; Yellon, D. M., Hausenloy, D. J., Myocardial reperfusion injury. *New England Journal of Medicine* 2007, 357:1121). It is postulated that the influx of calcium and the increase in free radicals triggers cell death, or programmed cell death (Chen, X., Zhang, X., Hubo, H., et al., $Ca^{2+}$ influx-induced sarcoplasmic reticulum $Ca^{2+}$ overload causes mitochondrial-dependent cell death in ventricular myocytes. *Circ Res* 2005, 97:1009; Lopes-Neblina, F., Toledo, A. H., Toledu-Pereyra, L. H. Molecular biology of apoptosis in ischemia and reperfusion. *J Invest Surg* 2005, 18:335). However, treatment of patients with acute myocardial infarction with antagonists that block the influx of calcium or with scavengers of the reactive oxygen species has yielded disappointing clinical outcomes (Yellon, D. M., Hausenloy, D. J., Myocardial reperfusion injury. *New England Journal of Medicine* 2007, 357:1121).

Another strategy for reducing ischemia-reperfusion injury is termed ischemic preconditioning. Short repeated bouts of ischemia followed by reperfusion will condition the myocardium to withstand a prolonged bout of ischemia (Otani, H., Ischemic preconditioning: From molecule mechanisms to therapeutic opportunities. *Antioxidants & Redox Signaling*, 2008, 10:207). However, intentionally occluding a patient's coronary artery is associated with undue risks and is therefore undesirable.

Thus, there is a significant need for new and more effective therapies and therapeutic agents for the treatment of ischemia and ischemia-reperfusion injuries resulting from cardiovascular disease and other conditions.

SUMMARY OF THE INVENTION

The invention described herein addresses a need for treating ischemia, ischemic injury and ischemia-reperfusion injury, including myocardial ischemia. In particular, the present invention relates to compositions comprising the disclosed compounds, or pharmaceutically acceptable salts or prodrugs thereof, and methods of using the disclosed compounds, or pharmaceutically acceptable salts or prodrugs thereof, to treat ischemia, ischemic injury, ischemia-reperfusion injury, and related conditions.

The compounds of the present invention are represented by Structural Formula (I):

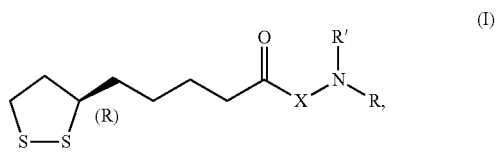

or a pharmaceutically acceptable salt or prodrug thereof, substantially separated from the (S)-lipoyl stereoisomer(s), or a pharmaceutically acceptable salt or prodrug thereof wherein:

R is $(C_1-C_{18})$alkyl, $(C_6-C_{18})$aryl or $(C_6-C_{18})$aryl$(C_1-C_{18})$alkyl and is substituted with at least one acidic substituent selected from the group consisting of —$CO_2H$, —$SO_3H$, —$PO_3H_2$, —$OSO_3H$, —$OPO_3H_2$, —$B(OH)_2$ and —NHOH, wherein the aryl of the $(C_6-C_{18})$aryl or $(C_6-C_{18})$aryl$(C_1-C_{18})$alkyl is optionally further substituted with one or more substituents selected from the group consisting of hydroxy, halo, $(C_1-C_3)$alkyl, halo$(C_1-C_3)$alkyl, cyano, nitro, $(C_1-C_3)$alkoxy and thio$(C_1-C_3)$alkyl;

R' is hydrogen or $(C_1-C_{18})$alkyl, wherein $(C_1-C_{18})$alkyl is optionally substituted with one or more acidic substituents selected from the group consisting of —$CO_2H$, —$SO_3H$, —$PO_3H_2$, —$OSO_3H$, —$OPO_3H_2$, —$B(OH)_2$ and —NHOH; and X is absent or is an amino acid, wherein the amino acid is oriented to form an amide linkage with

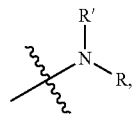

provided that the compound of Structural Formula (I) is not N-(R)-lipoyl-glutamylalanine, N-(R)-lipoyl-aminoethylphosphonic acid, or (R)-5-(5-(1,2-dithiolan-3-yl)pentanamido)-2-hydroxybenzoic acid.

The present invention also provides a method of treating ischemic injury or ischemia-reperfusion injury in a subject in need thereof, comprising administering to the subject an effective amount of a compound represented by Structural Formula (Ia):

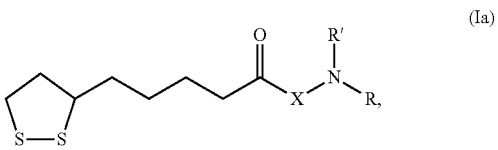

or a pharmaceutically acceptable salt or prodrug thereof, wherein:

R is $(C_1-C_{18})$alkyl, $(C_6-C_{18})$aryl or $(C_6-C_{18})$aryl$(C_1-C_{18})$alkyl and is substituted with at least one acidic substituent selected from the group consisting of —CO$_2$H, —SO$_3$H, —PO$_3$H$_2$, —OSO$_3$H, —OPO$_3$H$_2$, —B(OH)$_2$ and —NHOH, wherein the aryl of the (C$_6$-C$_{18}$)aryl or (C$_6$-C$_{18}$)aryl(C$_1$-C$_{18}$)alkyl is optionally further substituted with one or more substituents selected from the group consisting of hydroxy, halo, (C$_1$-C$_3$)alkyl, halo(C$_1$-C$_3$)alkyl, cyano, nitro, (C$_1$-C$_3$)alkoxy and thio(C$_1$-C$_3$)alkyl;

R' is hydrogen or (C$_1$-C$_{18}$)alkyl, wherein (C$_1$-C$_{18}$)alkyl is optionally substituted with one or more acidic substituents selected from the group consisting of —CO$_2$H, —SO$_3$H, —PO$_3$H$_2$, —OSO$_3$H, —OPO$_3$H$_2$, —B(OH)$_2$ and —NHOH; and X is absent or is an amino acid, wherein the amino acid is oriented to form an amide linkage with

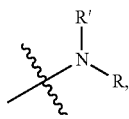

provided that the compound of Structural Formula (Ia) is not N-lipoyl-glutamylalanine, N-lipoyl-aspartylglycine, N-lipoyl-glutamylglycine or 5-(5-(1,2-dithiolan-3-yl)pentanamido)-2-hydroxybenzoic acid.

In another embodiment, the invention relates to a method of inhibiting cell death in a subject, comprising administering to the subject an effective amount of a compound represented by Structural Formula (I) and/or (Ia), or a pharmaceutically acceptable salt or prodrug thereof.

In yet another embodiment, the invention relates to a method of inhibiting cell death in a cell, tissue or organ, wherein the cell, tissue or organ has experienced an ischemia or other condition or disorder that results in excessive or unwanted cell death, comprising administering to the cell, tissue or organ an effective amount of a compound represented by Structural Formula (I) and/or (Ia), or a pharmaceutically acceptable salt or prodrug thereof.

Also included in the present invention is the use of a compound represented by Structural Formula (I) and/or (Ia), or a pharmaceutically acceptable salt or prodrug thereof, for treating ischemic injury or ischemia-reperfusion injury in a subject.

In another embodiment, the invention relates to the use of a compound represented by Structural Formula (I) and/or (Ia), or a pharmaceutically acceptable salt or prodrug thereof, for inhibiting cell death in a subject.

The present invention also includes the use of a compound represented by Structural Formula (I) and/or (Ia), or a pharmaceutically acceptable salt or prodrug thereof, for the manufacture of a medicament for treating ischemic injury or ischemia-reperfusion injury in a subject.

The invention also includes the use of a compound represented by Structural Formula (I) and/or (Ia), or a pharmaceutically acceptable salt or prodrug thereof, for the manufacture of a medicament for inhibiting cell death in a subject.

The compounds (also referred to herein as "the disclosed compounds"), compositions and methods of the present invention are efficacious for treating tissue damage resulting from ischemia and ischemic injuries, including ischemia-reperfusion injuries.

DETAILED DESCRIPTION OF THE INVENTION

Definitions

The disclosed compounds may exist in various stereoisomeric forms unless otherwise specified. "Stereoisomers" are compounds that differ only in their spatial arrangement.

"Enantiomers" are pairs of stereoisomers that are non-superimposable mirror images of one another, most commonly because they contain an asymmetrically substituted carbon atom that acts as a chiral center.

"Diastereomers" are stereoisomers that are not related as mirror images, most commonly because they contain two or more asymmetrically substituted carbon atoms. "R" and "S" represent the configuration of substituents around one or more chiral carbon atoms.

"Racemate" or "racemic mixture," as used herein, refers to a mixture containing equimolar quantities of two enantiomers of a compound. Such mixtures exhibit no optical activity (i.e., they do not rotate a plane of polarized light).

Percent enantiomeric excess (ee) is defined as the absolute difference between the mole fraction of each enantiomer multiplied by 100% and can be represented by the following equation:

$$ee = \left| \frac{R-S}{R+S} \right| \times 100\%,$$

where R and S represent the respective fractions of each enantiomer in a mixture, such that R+S=1. When a single enantiomer is named or depicted by structure, the depicted or named enantiomer is present in an ee of at least or about 50%, about 60%, about 70%, about 80%, about 90%, about 95%, about 98%, about 99% or about 99.9%.

Percent diastereomeric excess (de) is defined as the absolute difference between the mole fraction of each diastereomer multiplied by 100% and can be represented by the following equation:

$$de = \left| \frac{D1 - (D2+D3+D4\ ...)}{D1 + (D2+D3+D4\ ...)} \right| \times 100\%,$$

where D1 and (D2+D3+D4 . . . ) represent the respective fractions of each diastereomer in a mixture, such that D1+(D2+D3+D4 . . . )=1. When a single diastereomer is named or depicted by structure, the depicted or named diastereomer is present in a de of at least or about 50%, about 60%, about 70%, about 80%, about 90%, about 95%, about 98%, about 99% or about 99.9%.

When a disclosed compound is named or depicted by structure without indicating the stereochemistry, and the compound has one chiral center, it is to be understood that the name or structure encompasses one enantiomer of the compound substantially separated from the corresponding optical isomer, a racemic mixture of the compound and mixtures enriched in one enantiomer relative to its corresponding optical isomer.

When a disclosed compound is named or depicted by structure without indicating the stereochemistry and has two or more chiral centers, it is to be understood that the name or structure encompasses a diastereomer substantially separated from other diastereomers, a pair of diastereomers substantially separated from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

"(R)-Lipoyl" refers to a compound containing a lipoyl moiety, wherein the stereocenter in the lipoyl moiety is in the (R) configuration. An (R)-lipoyl moiety is pictured below:

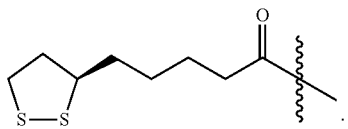 [SMILES: *C(=O)CCCC[C@@H]1CCSS1]

An example of an (R)-lipoyl compound is shown below:

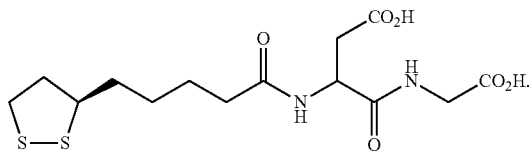 [SMILES: O=C(O)CNC(=O)C(CC(=O)O)NC(=O)CCCC[C@@H]1CCSS1]

"(S)-Lipoyl" refers to a compound containing a lipoyl moiety, wherein the stereocenter in the lipoyl moiety is in the (S) configuration. An (S)-lipoyl moiety is pictured below:

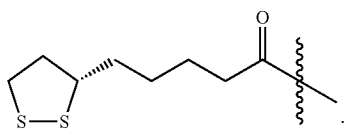 [SMILES: *C(=O)CCCC[C@H]1CCSS1]

An example of an (S)-lipoyl compound is shown below:

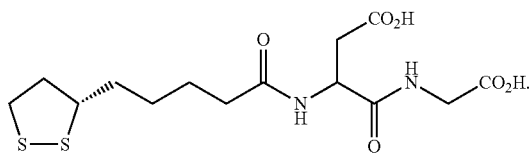 [SMILES: O=C(O)CNC(=O)C(CC(=O)O)NC(=O)CCCC[C@H]1CCSS1]

"Alkyl" means a saturated aliphatic branched or straight-chain monovalent hydrocarbon radical having the specified number of carbon atoms. Thus, "$(C_1-C_6)$alkyl" means a radical having from 1-6 carbon atoms in a linear or branched arrangement. "$(C_1-C_6)$alkyl" includes methyl, ethyl, propyl, i-propyl, butyl, i-butyl, t-butyl, sec-butyl, pentyl and hexyl. Typically, alkyl has 1 to 20, 1 to 15, 1 to 10, 1 to 5 or 1 to 3 carbon atoms.

One or more hydrogen atoms of an alkyl group can be replaced with a substituent group. Suitable substituent groups include hydroxy, thio, halo, halo($C_1$-$C_3$)alkyl, ($C_1$-$C_3$)alkoxy and thio($C_1$-$C_3$)alkyl. Preferred alkyl substituent groups include hydroxy and halo. An alkyl can also be substituted with one or more acidic substituents selected from the group consisting of $-CO_2H$, $-SO_3H$, $-PO_3H_2$, $-OSO_3H$, $-OPO_3H_2$, $-B(OH)_2$ and $-NHOH$.

The term "alkoxy" means $-O$-alkyl, where alkyl is as defined above.

The term "halogen" means F, Cl, Br or I.

The term "aryl" means a carbocyclic aromatic ring. "($C_6$-$C_{14}$)aryl" includes phenyl, napthyl, indenyl, and anthracenyl. Typically, aryl has 6 to 20, 6 to 14, 6 to 10, 6 to 9, or 6 carbon atoms.

As used herein, "substantially separated" or "substantially pure" means that the ee or de of the depicted or named compound is at least about 50%. For example, "substantially separated" or "substantially pure" can mean the ee or de of the depicted or named enantiomer is at least or about 50%, about 60%, about 70%, about 80%, about 90%, about 95%, about 98%, about 99% or about 99.9%. In one embodiment, substantially separated or substantially pure means that the ee or de of the depicted or named compound is at least or about 75%. In a specific embodiment, substantially separated means that the ee or de of the depicted or named compound is at least or about 90%. In a more specific embodiment, substantially separated means that the ee or de of the depicted or named compound is at least or about 95%. In yet a more specific embodiment, substantially separated means that the ee or de of the depicted or named compound is at least or about 99%. In another specific embodiment, substantially separated means that the ee or de of the depicted or named compound is at least or about 99.9%.

As used herein, the term "amino acid" means a molecule containing an amine group, a carboxylic acid group and a side chain which varies between different amino acids and includes both naturally-occurring amino acids and non-naturally-occurring amino acids. In one embodiment, "amino acid" is used to refer to naturally-occurring amino acids.

As used herein, the term "naturally-occurring amino acid" means a compound represented by the formula $NH_2$—CHR—COOH, wherein R is the side chain of a naturally-occurring amino acid such as an amino acid listed or named in the Table below. "Naturally-occurring amino acid" includes both the D- and L-configuration. When an amino acid is named or depicted by structure without indicating the stereochemistry and has at least one chiral center, it is to be understood that the name or structure encompasses a single enantiomer or diastereomer substantially separated from the other enantiomer or diastereomer, in which the one enantiomer or diastereomer is enriched relative to the other enantiomer or diastereomer(s), a racemic or diastereomeric mixture of the enantiomer or diastereomer(s) and mixtures enriched in one enantiomer or diastereomer relative to its corresponding optical isomer or other diastereomer(s).

Table of Common Naturally Occurring Amino Acids

| | Amino acid | Three letter code | One letter code |
|---|---|---|---|
| Non-polar; neutral at pH 7.4 | alanine | Ala | A |
| | isoleucine | Ile | I |
| | leucine | Leu | L |
| | methionine | Met | M |
| | phenylalanine | Phe | F |
| | proline | Pro | P |
| | tryptophan | Trp | W |
| | valine | Val | V |
| Polar, uncharged at pH 7.0 | asparagine | Asn | N |
| | cysteine | Cys | C |
| | glycine | Gly | G |
| | glutamine | Gln | Q |
| | serine | Ser | S |
| | threonine | Thr | T |
| | tyrosine | Tyr | Y |
| Polar; charged at pH 7 | glutamic acid | Glu | E |
| | arginine | Arg | R |
| | aspartic acid | Asp | D |
| | histidine | His | H |
| | lysine | Lys | K |

"Non-natural amino acid" means an amino acid for which there is no nucleic acid codon. Examples of non-natural amino acids include natural α-amino acids with non-natural side chains (e.g., entry 6 and 7 in Table 2); β-amino acids (e.g., β-alanine); γ-amino acids (e.g., γ-aminobutryric acid).

As used herein, an "effective amount" is an amount sufficient to achieve a desired therapeutic or prophylactic effect in a subject in need thereof under the conditions of administration, such as, for example, an amount sufficient to inhibit (e.g., prevent, delay) ischemia and ischemia-reperfusion injury in a subject (e.g., by inhibiting cell death of one or more affected cells in the subject). The effectiveness of a therapy can be determined by suitable methods known by those of skill in the art. An effective amount includes any amount of a compound (e.g., a compound of Structural Formula (I) and/or (Ia)) which prevents the onset of, alleviates the symptoms of, or stops the progression of a disorder or disease being treated (e.g., ischemia or ischemia-reperfusion injury) in a subject.

The term "treating" is defined as administering to a subject in need thereof an effective amount of a compound (e.g., of Structural Formula (I) and/or (Ia), or a pharmaceutically acceptable salt or prodrug thereof) that is sufficient to prevent the onset of, alleviate the symptoms of, or stop the progression of a disorder or disease being treated.

The term "subject," as used herein, refers to a mammal. In a preferred embodiment, the subject is a human.

Compounds of the Invention

The present invention relates in one embodiment to a compound represented by Structural Formula (I) and/or (Ia).

R is $(C_1\text{-}C_{18})$alkyl, $(C_6\text{-}C_{18})$aryl or $(C_6\text{-}C_{18})$aryl$(C_1\text{-}C_{18})$alkyl and is substituted with at least one acidic substituent selected from the group consisting of —$CO_2H$, —$SO_3H$, —$PO_3H_2$, —$OSO_3H$, —$OPO_3H_2$, —$B(OH)_2$ and —NHOH, wherein the aryl of the $(C_6\text{-}C_{18})$aryl or $(C_6\text{-}C_{18})$aryl$(C_1\text{-}C_{18})$alkyl is optionally further substituted with one or more substituents selected from the group consisting of hydroxy, halo, $(C_1\text{-}C_3)$alkyl, halo$(C_1\text{-}C_3)$alkyl, cyano, nitro, $(C_1\text{-}C_3)$alkoxy and thio$(C_1\text{-}C_3)$alkyl.

In one embodiment, R is $(C_1\text{-}C_{18})$alkyl. In another embodiment, R is $(C_1\text{-}C_3)$alkyl. In a further embodiment, R is $(C_3)$alkyl. In a further embodiment, R is $(C_2)$alkyl. Alternatively, R is $(C_1)$alkyl.

In another embodiment, R is $(C_6\text{-}C_{18})$aryl. In a further embodiment, R is $(C_6)$aryl.

In another embodiment, R is $(C_6\text{-}C_{18})$aryl$(C_1\text{-}C_{18})$alkyl. In a further embodiment, R is $(C_6)$aryl$(C_1\text{-}C_3)$alkyl. Alternatively, R is $(C_6)$aryl$(C_1\text{-}C_2)$alkyl.

In another embodiment, R is $(C_6)$aryl$(C_2)$alkyl. In a further embodiment, R is $(C_6)$aryl$(C_1)$alkyl.

The at least one acidic substituent is selected from the group consisting of —$CO_2H$, —$SO_3H$, —$PO_3H_2$, —$OSO_3H$, —$OPO_3H_2$, —$B(OH)_2$ and —NHOH. In one embodiment, the at least one acidic substituent is selected from the group consisting of —$CO_2H$, —$SO_3H$, —$PO_3H_2$, —$OSO_3H$ and —$OPO_3H_2$.

R is substituted with at least one acidic substituent selected from the group consisting of —$CO_2H$, —$SO_3H$, —$PO_3H_2$, —$OSO_3H$, —$OPO_3H_2$, —$B(OH)_2$ and —NHOH. In one embodiment, R is substituted with one, two or three acidic substituents. In a further embodiment, R is substituted with one or two acidic substituents.

Aryl is optionally further substituted with one or more substituents selected from the group consisting of hydroxy, halo, $(C_1\text{-}C_3)$alkyl, halo$(C_1\text{-}C_3)$alkyl, cyano, nitro, $(C_1\text{-}C_3)$alkoxy and thio$(C_1\text{-}C_3)$alkyl. In one embodiment, aryl is further substituted with one, two or three substituents. In another embodiment, aryl is substituted with one substituent. Alternatively, aryl is unsubstituted. In a further embodiment, aryl is further substituted with one or more substituents selected from the group consisting of hydroxyl and halo.

R' is hydrogen or $(C_1\text{-}C_{18})$alkyl, wherein said $(C_1\text{-}C_{18})$ alkyl is optionally substituted with one or more acidic substituents selected from the group consisting of —$CO_2H$, —$SO_3H$, —$PO_3H_2$, —$OSO_3H$, —$OPO_3H_2$, —$B(OH)_2$ and —NHOH. In one embodiment, R' is hydrogen.

In one embodiment, R' is $(C_1\text{-}C_{18})$alkyl. In another embodiment, R' is $(C_1\text{-}C_3)$alkyl. In a further embodiment, R' is $(C_3)$alkyl. In a further embodiment, R' is $(C_2)$alkyl. Alternatively, R' is $(C_1)$alkyl.

R' is substituted with at least one acidic substituent selected from the group consisting of —$CO_2H$, —$SO_3H$, —$PO_3H_2$, —$OSO_3H$, —$OPO_3H_2$, —$B(OH)_2$ and —NHOH. In one embodiment, R' is substituted with one, two or three acidic substituents. In another embodiment, R' is substituted with one or two acidic substituents. In a further embodiment, R' is substituted with one acidic substituent. Alternatively, R' is unsubstituted.

X is absent or an amino acid, wherein the amino acid is oriented to form an amide linkage with

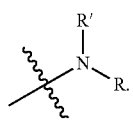

For example, the moiety in N-lipoyl-glutamylalanine is oriented as shown in Structural Formula below:

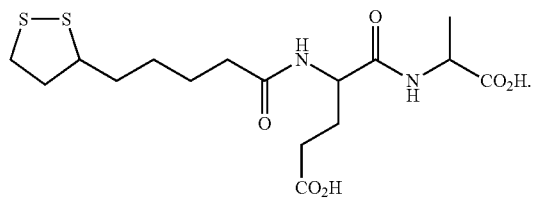 [SMILES: CC(NC(=O)C(CCC(=O)O)NC(=O)CCCCC1CCSS1)C(=O)O]

In one embodiment, X is absent. Alternatively, X is an amino acid. In a further embodiment, X is a naturally-occurring amino acid. In yet a further embodiment, X is aspartic acid, tyrosine, glutamic acid or alanine.

The compounds of Structural Formulas (I) and/or (Ia) are not N-(R)-lipoyl-glutamylalanine, N-lipoyl-aspartylglycine, N-lipoyl-glutamylglycine, N-(R)-lipoyl-aminoethylphosphonic acid, or (R)-5-(5-(1,2-dithiolan-3-yl)pentanamido)-2-hydroxybenzoic acid.

The compounds of Structural Formulas (I) and/or (Ia) are not N-lipoyl-glutamylalanine, N-lipoyl-aspartylglycine, N-lipoyl-glutamylglycine, N-lipoyl-glutamine, N-lipoyl-glycine or 5-(5-(1,2-dithiolan-3-yl)pentanamido)-2-hydroxybenzoic acid.

In addition, in specific embodiments, the compound of Structural Formulas (I) and/or (Ia) is not N-lipoyl-aspartylalanine.

In a $1^{st}$ specific embodiment, the compound is represented by Structural Formula (I) and/or (Ia), wherein the values and alternative values for the variables are as described above.

In a first aspect of the $1^{st}$ specific embodiment of the present invention, the (R)-lipoyl stereoisomer of a compound represented by Structural Formulas (I) or (Ia), or a pharmaceutically acceptable salt or prodrug thereof, is substantially separated from the (S)-lipoyl stereoisomer(s) or a pharmaceutically acceptable salt or prodrug thereof. Values and alternative values for the remainder of the variables are as described above for Structural Formulas (I) or (Ia) or in the 1st specific embodiment.

In a second aspect of the 1st specific embodiment of the present invention, R' is H. Values and alternative values for the remainder of the variables are as described above for Structural Formulas (I) or (Ia) or in the 1st specific embodiment, or first aspect thereof.

In a third aspect of the 1st specific embodiment of the present invention, R' is H and X is a naturally-occurring amino acid. Values and alternative values for the remainder of the variables are as described above for Structural Formulas (I) or (Ia) or in the 1st specific embodiment, or first or second aspect thereof.

In a fourth aspect of the 1st specific embodiment of the present invention, R and R' are each ($C_1$-$C_3$)alkyl substituted with one or two acidic substituents each independently selected from —$CO_2H$, —$SO_3H$, —$PO_3H_2$, —$OSO_3H$ and —$OPO_3H_2$. Values and alternative values for the remainder of the variables are as described above for Structural Formulas (I) or (Ia) or in the 1st specific embodiment, or first to third aspects thereof.

In a fifth aspect of the 1st specific embodiment of the present invention, R' is H and X is absent. Values and alternative values for the remainder of the variables are as described above for Structural Formulas (I) or (Ia) or in the 1st specific embodiment, or first to fourth aspects thereof.

In a sixth aspect of the 1st specific embodiment of the present invention, R is ($C_1$-$C_3$)alkyl substituted with one or two acidic substituents each independently selected from —$CO_2H$, —$SO_3H$, —$PO_3H_2$, —$OSO_3H$ and —$OPO_3H_2$. Values and alternative values for the remainder of the variables are as described above for Structural Formulas (I) or (Ia) or in the 1st specific embodiment, or first to fifth aspects thereof.

In a seventh aspect of the 1st specific embodiment of the present invention, R is ($C_6$)aryl($C_1$-$C_3$)alkyl substituted with one or two acidic substituents each independently selected from —$CO_2H$, —$SO_3H$, —$PO_3H_2$, —$OSO_3H$ and —$OPO_3H_2$. Values and alternative values for the remainder of the variables are as described above for Structural Formulas (I) or (Ia) or in the 1st specific embodiment, or first to sixth aspects thereof.

In an eighth aspect of the 1st specific embodiment of the present invention, R is ($C_2$)alkyl substituted with one or two acidic substituents each independently selected from —$CO_2H$, —$SO_3H$, —$PO_3H_2$, —$OSO_3H$ and —$OPO_3H_2$. Values and alternative values for the remainder of the variables are as described above for Structural Formulas (I) or (Ia) or in the 1st specific embodiment, or first to seventh aspects thereof.

In a ninth aspect of the 1st specific embodiment of the present invention, R is ($C_6$)aryl substituted with one acidic substituent selected from —$CO_2H$, —$SO_3H$, —$PO_3H_2$, —$OSO_3H$ and —$OPO_3H_2$. Values and alternative values for the remainder of the variables are as described above for Structural Formulas (I) or (Ia) or in the 1st specific embodiment, or first to eighth aspects thereof.

In a tenth aspect of the 1st specific embodiment of the present invention, the compound represented by Structural Formulas (I) and/or (Ia) is not N-lipoyl-glutamylalanine, N-lipoyl-aspartylglycine, N-lipoyl-glutamylglycine or 5-(5-(1,2-dithiolan-3-yl)pentanamido)-2-hydroxybenzoic acid. Values and alternative values for the remainder of the variables are as described above for Structural Formulas (I) or (Ia) or in the 1st specific embodiment, or first to ninth aspects thereof.

In an eleventh aspect of the 1st specific embodiment of the present invention, the compound represented by Structural Formulas (I) and/or (Ia) is not N-lipoyl-glutamylalanine, N-lipoyl-aspartylglycine, N-lipoyl-glutamylglycine, N-lipoyl-glutamic acid, N-lipoyl-aspartic acid, N-lipoyl-glycine or 5-(5-(1,2-dithiolan-3-yl)pentanamido)-2-hydroxybenzoic acid. Values and alternative values for the remainder of the variables are as described above for Structural Formulas (I) or (Ia) or in the 1st specific embodiment, or first to tenth aspects thereof.

In a twelfth aspect of the 1st specific embodiment of the present invention, the compound of Structural Formula (I) is not N-(R)-lipoyl-glutamylalanine, N-(R)-lipoyl-aspartylglycine, N-(R)-lipoyl-aminoethylphosphonic acid, or (R)-5-(5-(1,2-dithiolan-3-yl)pentanamido)-2-hydroxybenzoic acid. Values and alternative values for the remainder of the variables are as described above for Structural Formulas (I) or (Ia) or in the 1st first specific embodiment, or first to eleventh aspects thereof.

In a thirteenth aspect of the first specific embodiment, the compound is represented by Structural Formula (I), wherein the values and alternative values are as described above for Structural Formulas (I) or (Ia) or in the 1st specific embodiment, or first to twelfth aspects thereof.

In a fourteenth aspect of the 1st specific embodiment, the compound is represented by Structural Formula (Ia), wherein the values and alternative values are as described above for Structural Formulas (I) or (Ia) or in the 1st specific embodiment, or first to thirteenth aspects thereof.

In a $2^{nd}$ specific embodiment, the compound is represented by one of the following structural formulas:

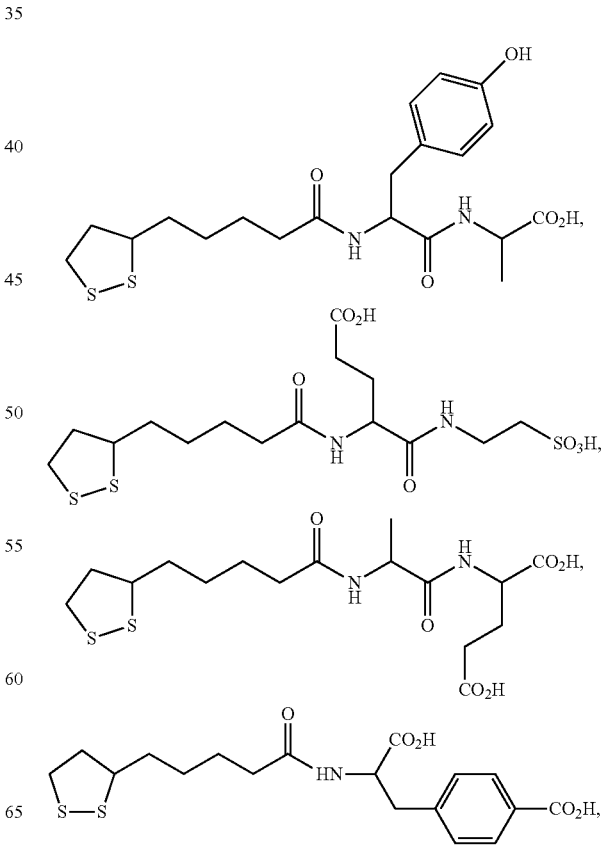

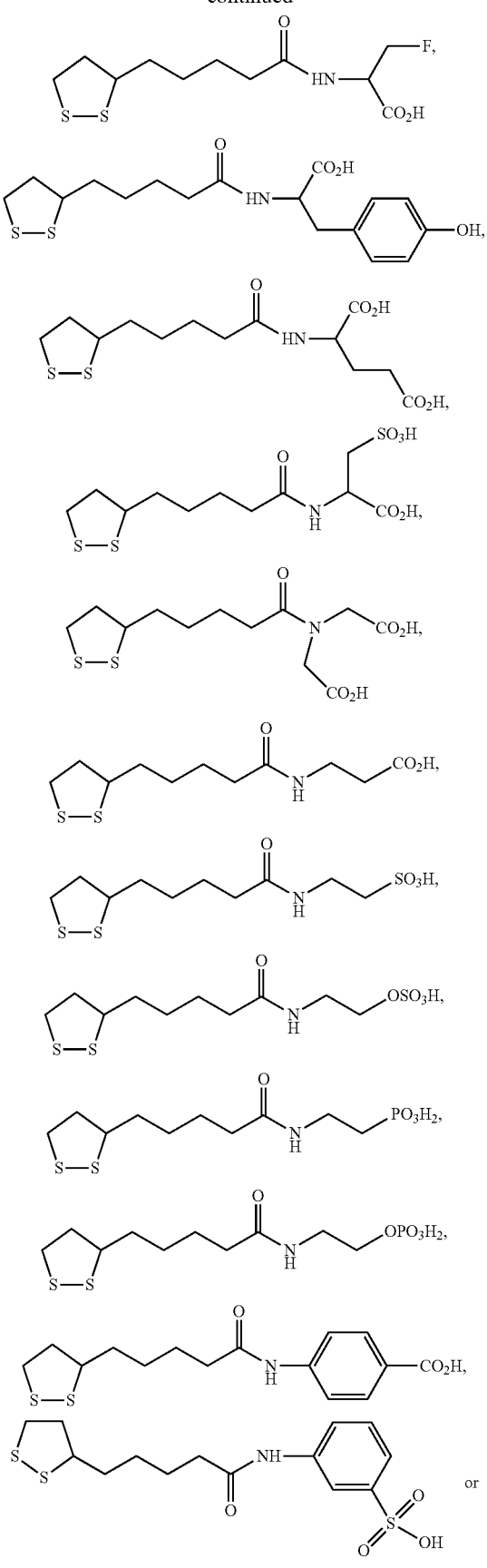

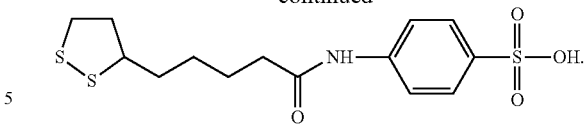

Values and alternative values for the remainder of the variables are as described above for Structural Formulas (I) or (Ia) or in the 1$^{st}$ specific embodiment, or aspects thereof.

In a first aspect of the 2$^{nd}$ specific embodiment of the present invention, the (R)-lipoyl stereoisomer of a compound represented by Structural Formulas (I) or (Ia), or a pharmaceutically acceptable salt or prodrug thereof, is substantially separated from the (S)-lipoyl stereoisomer(s) or a pharmaceutically acceptable salt or prodrug thereof. Values and alternative values for the remainder of the variables are as described above for Structural Formula (Ia), in the 1$^{st}$ specific embodiment, or aspects thereof, or in the 2$^{nd}$ specific embodiment.

The invention also relates to pharmaceutically acceptable salts of the disclosed compounds of the present invention. The term "pharmaceutically acceptable salts" embraces salts commonly used to form alkali metal salts and to form addition salts of free bases. The nature of the salt is not critical, provided that it is pharmaceutically acceptable.

The pharmaceutically acceptable salts of the compounds of the present invention include base addition salts. Suitable pharmaceutically acceptable base addition salts of compounds of the present invention include, but are not limited to, metallic salts made from aluminum, calcium, lithium, magnesium, potassium, sodium and zinc or organic salts made from N,N'-dibenzylethylene-diamine, chloroprocaine, choline, diethanolamine, ethylenediamine, N-methylglucamine, lysine and procaine. All of these salts may be prepared by conventional means from a corresponding compound of the present invention by treating, for example, a compound of Tables 1-5 with the appropriate acid or base.

In one embodiment, the pharmaceutically acceptable salt comprises a monovalent or divalent cation. As used herein, "cation" refers to an atom or molecule that has a positive charge. A cation can be, for example, a metal or an amine. In a particular embodiment, the cation is a metal cation, such as a sodium cation.

As used herein, "amine salt" relates to a cation containing a protonated amino group. Amine salts include amino acid salts, such as lysine salts. In another embodiment, the cation is an amine and the pharmaceutically acceptable salt is an amine salt. In a particular embodiment, the pharmaceutically acceptable salt comprises lysine.

Salts can be chiral. When a disclosed salt has at least one chiral center and is named or depicted by structure without indicating the stereochemistry, it is to be understood that the name or structure encompasses one stereoisomer or enantiomer of the compound free from the corresponding stereoisomer(s) or enantiomer, a racemic mixture of the compound, or mixtures enriched in one stereoisomer or enantiomer relative to its corresponding stereoisomer(s) or enantiomer.

The invention also relates to pharmaceutically acceptable prodrugs of the disclosed compounds of the present invention.

In one embodiment, the invention relates to the compounds of Structural Formulas (I) and/or (Ia), wherein the hydrogen of each acidic functionality (e.g., —COOH, —SO$_3$H, —OSO$_3$H, —PO(OH)$_2$, —OPO(OH)$_2$) is optionally and independently replaced with a hydrolyzable group. The invention also encompasses pharmaceutically acceptable salts of the compounds including said hydrolyzable groups.

As used herein, the term "hydrolyzable group" refers to a moiety that, when present in a molecule of the invention, yields a carboxylic acid, or salt thereof, upon hydrolysis. Hydrolysis can occur, for example, spontaneously under acidic or basic conditions in a physiological environment (e.g., blood, metabolically active tissues, for example, liver, kidney, lung, brain), or can be catalyzed by an enzyme(s), (e.g., esterase, peptidases, hydrolases, oxidases, dehydrogenases, lyases or ligases). A hydrolyzable group can confer upon a compound of the invention advantageous properties in vivo, such as improved water solubility, improved circulating half-life in the blood, improved uptake, improved duration of action, or improved onset of action.

In one embodiment, the hydrolyzable group does not destroy the biological activity of the compound. In an alternative embodiment, a compound with a hydrolyzable group can be biologically inactive, but can be converted in vivo to a biologically active compound.

Compounds of the invention that include hydrolyzable groups may act as prodrugs. As used herein, the term "prodrug" means a compound that can be hydrolyzed, oxidized, metabolized or otherwise react under biological conditions to provide a compound of the invention. Prodrugs may become active upon such reaction under biological conditions, or they may have activity in their unreacted forms. A prodrug may undergo reduced metabolism under physiological conditions (e.g., due to the presence of a hydrolyzable group), thereby resulting in improved circulating half-life of the prodrug (e.g., in the blood). Prodrugs can typically be prepared using well-known methods, such as those described by Burger's Medicinal Chemistry and Drug Discovery (1995) 172-178, 949-982 (Manfred E. Wolff ed., $5^{th}$ Ed).

In one embodiment, the hydrolyzable group is selected from the group consisting of $(C_1-C_{10})$alkyl, $(C_2-C_{10})$alkenyl, $(C_2-C_{10})$alkynyl, $(C_1-C_{10})$alkoxy$(C_1-C_{10})$alkyl, $(C_1-C_{10})$ alkoxy$(C_1-C_{10})$alkoxy$(C_1-C_{10})$alkyl, aryl and aryl$(C_1-C_{10})$ alkyl, wherein each is optionally substituted with 1 to 3 substituents selected from the group consisting of halo, nitro, cyano, cyclopropyl, cyclobutyl, cyclopentyl, cyclohexyl, amino, $(C_1-C_6)$alkylamino, di$(C_1-C_6)$alkylamino, $(C_1-C_6)$ alkyl, halo$(C_1-C_6)$alkyl, $(C_1-C_6)$alkoxy, halo$(C_1-C_6)$alkoxy, morpholino, phenyl, and benzyl.

In another embodiment, the hydrolyzable group is selected from the group consisting of methyl, ethyl, n-propyl, isopropyl, n-butyl, sec-butyl, isobutyl, tert-butyl, pentyl, hexyl, heptyl, allyl, ethoxymethyl, methoxyethyl, methoxyethoxymethyl, methoxyethoxyethyl, benzyl, pentafluorophenyl, 2-N-(morpholino)ethyl, dimethylaminoethyl and para-methoxybenzyl.

Methods

In another embodiment, the invention relates to a method for treating an ischemia or ischemia-reperfusion injury in a subject in need thereof, comprising administering to the subject an effective amount of one or more compounds of Structural Formulas (I) and/or (Ia), or a pharmaceutically acceptable salt or prodrug thereof, provided that the compounds of Structural Formula (I) are not N-(R)-lipoyl-glutamylalanine, N-(R)-lipoyl-aminoethylphosphonic acid, or (R)-5-(5-(1,2-dithiolan-3-yl)pentanamido)-2-hydroxybenzoic acid and the compounds of Structural Formula (Ia) are not N-lipoyl-glutamylalanine, N-lipoyl-aspartylglycine, N-lipoyl-glutamylglycine or 5-(5-(1,2-dithiolan-3-yl)pentanamido)-2-hydroxybenzoic acid. In some embodiments, the pharmaceutically acceptable salt is a lysine salt. In one embodiment, the salt is an L-lysine salt. In a particular embodiment, the ischemia or ischemia-reperfusion injury is a myocardial ischemia or ischemia-reperfusion injury. In another embodiment, the compound is administered as a composition comprising one or more compounds of the invention.

As used herein, the "injury resulting from ischemia," "injury caused by ischemia" and "ischemic injury" refer to an injury to a cell, tissue or organ caused by ischemia, or an insufficient supply of blood (e.g., due to a blocked artery), and thus oxygen, resulting in damage or dysfunction of the tissue or organ (Piper, H. M., Abdallah, C., Schafer, C., *Annals of Thoracic Surgery* 2003, 75:644; Yellon, D. M., Hausenloy, D. J., *New England Journal of Medicine* 2007, 357:1121). Injuries that result from ischemia can affect various tissues and organs. Such injuries may be treated by the compounds and methods of the invention, including, for example, injuries caused by cardiovascular ischemia, cerebrovascular ischemia, renal ischemia, hepatic ischemia, ischemic cardiomyopathy, cutaneous ischemia, bowel ischemia, intestinal ischemia, gastric ischemia, pulmonary ischemia, pancreatic ischemia, skeletal muscle ischemia, abdominal muscle ischemia, limb ischemia, ischemic colitis, mesenteric ischemia and silent ischemia. Thus, an injury resulting from ischemia can affect, for example, a heart, kidney, liver, brain, muscle, intestine, stomach, lung or skin.

In a particular embodiment, the injury resulting from ischemia is the result of a myocardial ischemia. An injury resulting from a myocardial ischemia can result from, for example, a myocardial infarction (e.g., an acute myocardial infarction) in a subject.

In another embodiment, the injury resulting from ischemia is an injury resulting from cerebral ischemia (e.g., a stroke) in a subject.

In another embodiment, the injury resulting from ischemia is an injury resulting from renal ischemia. An injury resulting from a renal ischemia can result from, for example, a deficiency of blood in one or both kidneys, or nephrons, usually due to functional constriction or actual obstruction of a blood vessel (e.g., an acute renal infarction) in a subject.

In another embodiment, the injury resulting from ischemia is an ischemia-reperfusion injury. As used herein, the term "ischemia-reperfusion injury" refers to an injury resulting from the restoration of blood flow to an area of a tissue or organ that had previously experienced deficient blood flow due to an ischemic event. Oxidative stresses associated with reperfusion may cause damage to the affected tissues or organs. Ischemia-reperfusion injury is characterized biochemically by a depletion of oxygen during an ischemic event followed by reoxygenation and the concomitant generation of reactive oxygen species during reperfusion (Piper, H. M., Abdallah, C., Schafer, C., *Annals of Thoracic Surgery* 2003, 75:644; Yellon, D. M., Hausenloy, D. J., *New England Journal of Medicine* 2007, 357:1121).

An ischemia-reperfusion injury can be caused, for example, by a natural event (e.g., restoration of blood flow following a myocardial infarction), a trauma, or by one or more surgical procedures or other therapeutic interventions that restore blood flow to a tissue or organ that has been subjected to a diminished supply of blood. Such surgical procedures include, for example, coronary artery bypass graft surgery, coronary angioplasty, organ transplant surgery and the like. In a particular embodiment, the compounds and methods of the invention are useful for treating peri-operative cardiac damage caused by an ischemia or ischemia-reperfusion injury.

For the treatment of ischemic and ischemia-reperfusion injuries caused by therapeutic interventions, such as surgical procedures, it is preferable that a compound of the invention is administered to a subject undergoing treatment prior to the therapeutic intervention (e.g., cardiac surgery, organ transplant). For example, a compound of the invention can be administered to a subject undergoing treatment, e.g., about 1 hour, about 2 hours, about 3 hours, about 4 hours, about 5 hours, about 12 hours, about 24 hours, or about 48 hours prior to the therapeutic intervention. A compound of the invention can also be administered to a subject undergoing treatment, for example, about 5 minutes, about 10 minutes, about 15 minutes, about 20 minutes, about 30 minutes or about 45 minutes prior to the therapeutic intervention.

Alternatively, or in addition, a compound of the invention can be administered to a subject undergoing treatment at the time of, or during, the therapeutic intervention. For example, the compound can be administered one or more times during the course of a therapeutic intervention in intervals (e.g., 15 minute intervals). Alternatively, a compound can be administered continuously throughout the duration of a therapeutic intervention.

Furthermore, a compound of the invention can be administered to a subject undergoing treatment after a therapeutic intervention. For example, a compound of the invention can be administered to a subject undergoing treatment, e.g., about 1 hour, about 2 hours, about 3 hours, about 4 hours, about 5 hours, about 12 hours, about 24 hours, or about 48 hours after the therapeutic intervention. A compound of the invention can also be administered to a subject undergoing treatment, for example, about 5 minutes, about 10 minutes, about 15 minutes, about 20 minutes, about 30 minutes or about 45 minutes after the therapeutic intervention.

A compound of the invention can also be used to inhibit an ischemia or ischemia-reperfusion injury to a cell, tissue or organ, ex vivo, prior to a therapeutic intervention (e.g., a tissue employed in a graft procedure, an organ employed in an organ transplant surgery). For example, prior to transplant of an organ into a host individual (e.g., during storage or transport of the organ in a sterile environment), the organ can be contacted with a compound of the invention (e.g., bathed in a solution comprising a compound of the invention) to inhibit ischemia or ischemia-reperfusion injury.

As described herein, conditions resulting from ischemia, and injuries caused by ischemia or ischemia-reperfusion, can induce cell death (e.g., apoptotic cell death) in an affected cell, tissue or organ, leading to damage and dysfunction. Accordingly, the compounds of the invention also have utility in methods of inhibiting cell death in a cell, a tissue or an organ (e.g., a transplant tissue or organ or a cell, tissue or organ in a subject), wherein the cell, tissue or organ has experienced an ischemia or other condition or disorder that results in excessive or unwanted cell death. The methods comprise contacting the cells, tissue, or organ in need thereof with, or administering to a subject in need thereof, an effective amount of one or more compounds of Structural Formulas (I) and/or (Ia), or a pharmaceutically acceptable salt or prodrug thereof.

In one embodiment, the invention relates to a method of inhibiting cell death (e.g., apoptotic cell death) in a subject, comprising administering to the subject an effective amount of a compound represented by Structural Formula (I) or (Ia), or a pharmaceutically acceptable salt or prodrug thereof.

Methods of assessing cell death are well known in the art. For example, microscopic analysis (e.g., light microscopy, electron microscopy, confocal microscopy, laser-scanning microscopy) for visualizing cell death (e.g., by detecting morphological changes associated with cell death, such as chromatin condensation and cytoplasmic shrinking) is typically employed to study cell death.

The study of DNA fragmentation in agarose gels is also considered to be indicative of apoptotic cell death. A number of techniques take advantage of DNA fragmentation for labeling the fragments and thus for quantifying the proportion of apoptotic cells. Each DNA fragment has a 3'-OH terminal portion. This terminal fragment can be labeled in various ways (for instance, with the help of a modified terminal deoxynucleotidyl transferase), so that the labeling rate is proportional to the degree of DNA fragmentation.

In particular, TdT-mediated dUTP Nick-End Labeling, or TUNEL, is a technique for detecting fragmented DNA, which occurs near the final step in the apoptotic process. Fragmented DNA of apoptotic cells can incorporate fluorescein-dUTP at 3'-OH at DNA ends using the enzyme Terminal Deoxynucleotidyl Transferase (TdT), which forms a polymeric tail using the principle of the TUNEL assay. The labeled DNA can then be visualized directly by fluorescence microscopy or quantitated by flow cytometry.

Some current techniques take advantage of the changes in membrane phospholipids that occur early in apoptotic cells. The negatively charged membrane phospholipids exposed to the external environment by the apoptotic cell are labeled with fluorochrome-conjugated molecules, and the percentage of fluorescent cells can be easily quantified.

Apoptosis can also be detected using fluorescently-conjugated Annexin V. Annexin V is an anticoagulant protein that preferentially binds negatively charged phospholipids. An early step in the apoptotic process is disruption of membrane phospholipid asymmetry, exposing phosphatidylserine (PS) on the outer leaflet of the cytoplasmic membrane. Fluorescently conjugated Annexin V can be used to detect this externalization of phosphatidylserine on intact living cells. Propidium iodide is often combined as a second flurochrome to detect necrotic cells. Induction of apoptosis leads to procaspase-3 proteolytic cleavage to generate an active 18 kDa caspase-3 fragment which then targets key modulators of the apoptotic pathway including poly-ADP-ribose polymerase and other caspases, for cleavage. Assays for detecting other active caspases in apoptotic cells are known in the art (e.g., Caspase-Glo® Assays, Promega).

Apoptotic cells can also be detected using the active 18 kDa caspase-3 fragment as a marker. Induction of apoptosis leads to procaspase-3 proteolytic cleavage to generate an active 18 kDa caspase-3 fragment which then targets key modulators of the apoptotic pathway, including poly-ADP-ribose polymerase and other caspases, for cleavage. Several antibodies that recognize only the active 18 kDa fragment are available from commercial suppliers (e.g., BD Biosciences, Chemicon, Cell Signaling Technology, Trevigen).

In addition, flow cytometry assays can be employed to monitor and quantify nuclear changes associated with apoptotic cells.

Conditions associated with unwanted and/or excess cell death that are treatable by the compounds and methods of the invention include, but are not limited to, neurodegenerative diseases associated with excess cell death (e.g., Parkinson's Disease, Alzheimer's Disease, amyotrophic lateral sclerosis, retinitis pigmentosa, epilepsy), haematologic diseases associated with excess cell death (e.g., aplastic anaemia, myelodysplastic syndrome, T CD4+ lymphocytopenia, G6PD deficiency), tissue damage associated with excess apoptosis (e.g., myocardial infarction, cerebrovascular accident, ischemic renal damage, polycystic kidney disease), AIDS, and preeclampsia.

The invention also relates to compositions comprising a pharmaceutical acceptable carrier or diluent and one or more of the disclosed compounds, or a pharmaceutically acceptable salt or prodrug thereof. The compositions disclosed herein are prepared in accordance with standard procedures and are administered at dosages that are selected to reduce, prevent, eliminate, or to slow or halt the progression of, the condition being treated. See, e.g., Remington's Pharmaceutical Sciences, 17th ed., Remington, J. P., Easton, Pa., Mack Publishing Company, 2005, and Goodman and Gilman's The Pharmaceutical Basis of Therapeutics, 12th ed., Brunton, L. et. als., eds., New York, McGraw-Hill, 2010, the contents of which are incorporated herein by reference, for a general description of the methods for administering various agents for human therapy. The compositions of the invention can be delivered using controlled or sustained-release delivery systems (e.g., capsules, bioerodable matrices). Exemplary delayed-release delivery systems for drug delivery that would be suitable for administration of the compositions of the present invention are described in U.S. Pat. No. 5,990,092 (issued to Walsh); U.S. Pat. No. 5,039,660 (issued to Leonard); U.S. Pat. No. 4,452,775 (issued to Kent); and U.S. Pat. No. 3,854,480 (issued to Zaffaroni).

The compositions of the present invention comprise one or more compounds of Structural Formulas (I) and/or (Ia), or a pharmaceutically acceptable salt or prodrug thereof, in association with one or more nontoxic, pharmaceutically acceptable carriers and/or diluents and/or adjuvants and/or excipients, collectively referred to herein as "carrier" materials, and optionally, other active ingredients. The compositions may contain from about 0.01% to about 99% by weight of the active ingredient, depending on the method of administration.

For preparing compositions from the compounds of the present invention, pharmaceutically acceptable carriers can either be solid or liquid. Solid form preparations include powders, tablets, pills, capsules, cachets, suppositories, and dispersible granules. For example, the compounds of the present invention may be in powder form for reconstitution at the time of delivery. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid which is in a mixture with the finely divided active ingredient.

In tablets, the active ingredient is mixed with the carrier having the necessary binding properties in suitable proportions and compacted in the shape and size desired.

The powders and tablets preferably contain from about one to about seventy percent of the active ingredient. Suitable carriers are magnesium carbonate, magnesium stearate, talc, sugar, lactose, pectin, dextrin, starch, gelatin, tragacanth, methylcellulose, sodium caboxymethylcellulose, a low-melting wax, cocoa butter, and the like. Tablets, powders, cachets, lozenges, fast-melt strips, capsules and pills can be used as solid dosage forms containing the active ingredient suitable for oral administration.

Liquid form preparations include solutions, suspensions, retention enemas, and emulsions, for example, water or water propylene glycol solutions. For parenteral injection, liquid preparations can be formulated in solution in aqueous polyethylene glycol.

Aqueous solutions suitable for oral administration can be prepared by dissolving the active ingredient in water and adding suitable colorants, flavors, stabilizing agents, and thickening agents as desired. Aqueous suspensions for oral administration can be prepared by dispersing the finely divided active ingredient in water with viscous material, such as natural or synthetic gums, resins, methylcellulose, sodium carboxymethylcellulose, and other well-known suspending agents.

Alternatively, the compounds or compositions of the present invention can be in powder form for reconstitution at the time of delivery.

The composition is preferably in unit dosage form. In such form, the composition is subdivided into unit doses containing appropriate quantities of the active ingredient. The unit dosage form can be a packaged preparation, the package containing discrete quantities of, for example, tablets, powders, and capsules in vials or ampules. Also, the unit dosage form can be a tablet, cachet, capsule, or lozenge itself, or it can be the appropriate amount of any of these in packaged form. The quantity of active ingredient in a unit dose preparation may be varied or adjusted from about 0.1 mg to about 1000 mg, preferably from about 0.1 mg to about 100 mg (e.g., for intravenous administration) or from about 1.0 mg to about 1000 mg (e.g., for oral administration). The dosages, however, may be varied depending upon the requirements of the subject, the severity of the condition being treated, the compound and the route of administration being employed. Determination of the proper dosage for a particular situation is within the skill in the art. In one embodiment, the dosage is from about 0.01 mg/kg to about 100 mg/kg.

In general, the methods for delivering the disclosed compounds and pharmaceutical compositions of the invention in vivo utilize art-recognized protocols for delivering the agent with the only substantial procedural modification being the substitution of the compounds represented by any one of the disclosed compounds for the drugs in the art-recognized protocols.

The compounds of the present invention may be administered by any route, preferably in the form of a composition adapted to such a route, and would be dependent on the condition being treated. The compounds and compositions may, for example, be administered intravascularly, intramuscularly, subcutaneously, intraperitoneally, intracardiacally, orally or topically. It will be obvious to those skilled in the art that the following dosage forms may comprise as the active ingredient, either compounds or a corresponding pharmaceutically acceptable salt of a compound of the present invention. Preferred methods of administration for the compounds of the invention include intravenous administration and oral administration.

For oral administration, the compositions may be in the form of, for example, a tablet, capsule, suspension or liquid. The composition is preferably made in the form of a dosage unit containing an effective amount of the active ingredient. Examples of such dosage units are tablets and capsules. For therapeutic purposes, the tablets and capsules can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants, for example, magnesium stearate, polyethylene glycol, silica, or talc; disintegrants, for example potato starch, flavoring or coloring agents, or acceptable wetting agents. Oral liquid preparations generally in the form of aqueous or oily solutions, suspensions, emulsions, syrups or elixirs may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

The compositions may also be administered parenterally via, for example, injection. Formulations for parenteral administration can be in the form of aqueous or non-aqueous isotonic sterile injection solutions or suspensions. These solutions or suspensions can be prepared from sterile powders or granules having one or more of the carriers mentioned for use in the formulations for oral administration. The compounds can be dissolved in polyethylene glycol, propylene glycol, ethanol, corn oil, benzyl alcohol, sodium chloride, and/or various buffers.

Delivery can also be by injection into the brain or body cavity of a patient or by use of a timed release or sustained release matrix delivery systems, or by onsite delivery using micelles, gels and liposomes. Nebulizing devices, powder inhalers, and aerosolized solutions are representative of methods that may be used to administer such preparations to the respiratory tract. Delivery can be in vitro, in vivo, or ex vivo.

The dosage regimen for treating an ischemia, ischemic injury or ischemia-reperfusion injury with a compound and/or composition of this invention is selected in accordance with a variety of factors, including the type, age, weight, sex and medical condition of the subject, the severity of the ischemia-reperfusion injury, the route and frequency of administration, and the particular compound or composition employed. In general, dosages are determined in accordance with standard practice for optimizing the correct dosage for treating ischemia-reperfusion injury-associated disease.

The dosages of a compound of the invention provided to a subject may be varied depending upon the requirements of the patient, the severity of the condition being treated, the route of administration and the compound being employed. Determination of the proper dosage for a particular situation is within the skill in the art. For example, suitable dosages for administration to humans can be extrapolated from data obtained in experiments performed on animal (e.g., rat) models. Guidance for extrapolating non-human animal model dosage data to human dosages can be found, for example, in *FDA Draft Guidance: Estimating the Safe Starting Dose in Clinical Trials for Therapeutics in Adult Healthy Volunteers* (2005).

For example, suitable intravenous dosages of a compound of the invention can be from about 0.001 mg/kg to about 100 mg/kg, from about 0.01 mg/kg to about 100 mg/kg, from about 0.01 mg/kg to about 10 mg/kg, from about 0.01 mg/kg to about 1 mg/kg body weight per treatment. Determining the dosage and route of administration for a particular agent, patient and ischemia or ischemia-reperfusion injury is well within the abilities of one of skill in the art. Preferably, the dosage does not cause or produces minimal adverse side effects.

An effective amount of a compound of the invention can be administered alone, or in combination with, one or more other therapeutic agents. Suitable therapeutic agents that are useful for treating ischemic injuries, which can be administered in combination with a compound of the invention, include, but are not limited to, calcium channel blockers, beta blockers, nitroglycerin, aspirin, anti-inflammatory agents, natriuretic factors, vasodilators, thrombolytic and antithrombotic agents.

Thus, a compound of the invention can be administered as part of a combination therapy (e.g., with one or more other therapeutic agents). The compound of the invention can be administered before, after or concurrently with one or more other therapeutic agents. In some embodiments, a compound of the invention and other therapeutic agent can be co-administered simultaneously (e.g., concurrently) as either separate formulations or as a joint formulation. Alternatively, the agents can be administered sequentially, as separate compositions, within an appropriate time frame, as determined by the skilled clinician (e.g., a time sufficient to allow an overlap of the pharmaceutical effects of the therapies). A compound of the invention and one or more other therapeutic agents can be administered in a single dose or in multiple doses, in an order and on a schedule suitable to achieve a desired therapeutic effect (e.g., a reduction in and/or inhibition of joint inflammation; a reduction in and/or inhibition of ischemia, a reduction in and/or inhibition of an ischemic injury; a reduction in and/or inhibition of an ischemia-reperfusion injury). Suitable dosages and regimens of administration can be determined by a clinician and are dependent on the agent(s) chosen, pharmaceutical formulation and route of administration, various patient factors and other considerations.

One of skill in the art can readily assess the efficacy of a compound for treating an ischemic injury or an ischemia-reperfusion injury by measuring biochemical or physiological parameters in the subject prior to and after treatment of the subject by using standard assays for the parameter(s) being measured. For example, the efficacy of a compound of the invention can be determined by analyzing the levels of surrogate cardiac biomarkers, including certain cardiac enzymes (e.g., creatine kinase (CK-MB), troponin-T, troponin-I), in blood samples obtained from a subject at various time points before and after the ischemic injury or ischemia-reperfusion injury, wherein a statistically significant reduction in the levels of the enzymes is indicative of the compound having efficacy in treating the injury. In an exemplary assessment, one or more blood samples are collected from a subject prior to the injury (e.g., about 6 to about 48 hours prior to the injury) and analyzed for CK-MB and troponin-T levels. Blood samples are then obtained from the subject at various time points after the injury (e.g., at 6.0, 12.0, 18.0, and 24.0 hours after the injury) and CK-MB and troponin-T levels are analyzed in one or more of these samples.

The efficacy of a compound of the invention can also be determined by electrocardiogram (ECG) monitoring. For example, standard continuous 12-lead ECG monitoring can be performed after fitting the subject with a continuous 12-lead ECG monitoring device with electronic data storage prior to dosing (e.g., about 5 minutes prior to dosing). The ECG readings can then be obtained before and after the injury (e.g., until about 24 hours after the injury). A change from an abnormal ECG trace to a normal ECG trace (e.g., a reduction of an elevated ST segment) is indicative of the compound having efficacy in treating the injury.

In addition, the efficacy of a compound of the invention can also be assessed by determining the ratio of the myocardial infarct area (MI) to the ischemic area at risk (AR), according to methods known in the art, wherein a statistically significant reduction of MI/AR ratio is indicative of the compound having efficacy in treating the injury.

EXEMPLIFICATION

Having described the invention generally, the inventors illustrate the invention with the following examples. These examples are merely illustrative of certain embodiments of the invention, which is not limited to exemplified embodiments.

Example 1

Representative Synthesis of Select Compounds of the Present Invention

Synthesis of rLip-Tau. rLipoic Acid (rLip-OH, 10.0 g) was dissolved in acetone (100 mL, 10 mL/g). The solution was protected from direct light by covering the reaction flask with foil. N,N-Disuccinimidylcarbonate (15.5 g, 1.25 equivalents) and N,N-diisopropylethylamine (DIEA, 10.5 mL, 1.25 equivalents) were added sequentially and the reaction was stirred vented for 2 hours at room temperature to form Lip-OSu in-situ. Taurine (7.0 g, 1.15 equivalents) was added to the solution of Lip-OSu in acetone, followed by the addition of water (50 mL) and DIEA (19.4 mL, 2.3 equivalents). The combined solution was stirred overnight. Approximately one third of the crude reaction mixture was transferred to a rotary evaporator and reduced to approximately half volume. The remaining reaction mixture was injected multiple times directly onto a semi-preparative high-performance liquid chromatography (HPLC) system and the product isolated on a YMC Pack Pro C18 reverse phase column using a gradient of increasing acetonitrile (0.5% acetic acid) in water (0.5% acetic acid). Product-containing fractions were identified by analytical HPLC, frozen, and lyophilized to provide 2.16 g Lip-Tau at >95% HPLC purity (percent area at 220 nm) as a gummy solid. The product $^1$H NMR was consistent with the assigned structure and the product had an observed mass of 312 (M−1), calculated 313.

Synthesis of rLip-Tau Lysine salt. The rLip-Tau (2.16 g) isolated by semi-preparative reverse phase chromatography and lyophilized was dissolved in 70 mL ethanol. Water (3.0 mL) was added to the ethanolic solution followed by L-lysine (1.33 g, 1 equivalent). The solution was shaken overnight, filtered, and rinsed 2 times with 15 mL ethanol. Isolated product was dried under vacuum to yield 3.1 g of the rLip-Tau Lysine salt with >95% HPLC purity (percent area at 220 nm). The product $^1$H NMR was consistent with the assigned structure.

The chemical name and structure of exemplary compounds of the invention are set forth in Table A. Table B contains nuclear magnetic resonance (NMR) data, high performance liquid chromatography (HPLC) data and mass spectroscopy data for the compounds in Table A.

TABLE A

Chemical Name and Structure of Exemplary Compounds of the Invention

| Entry | Chemical Name | Structure |
|---|---|---|
| A | RLip-Taurine-OH | 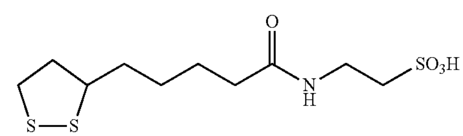 |
| B | RLip-Idaa | 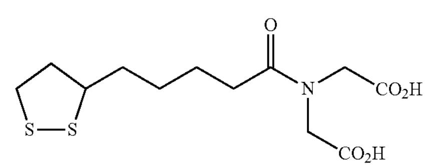 [SMILES: O=C(O)CN(CC(=O)O)C(=O)CCCCC1CCSS1] |
| C | RLip-E-OH | 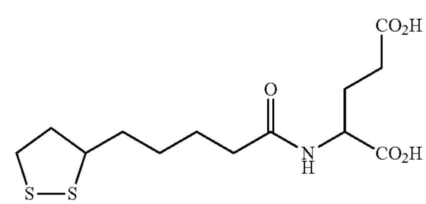 [SMILES: O=C(O)CCC(NC(=O)CCCCC1CCSS1)C(=O)O] |
| D | RLip-EG-OH | 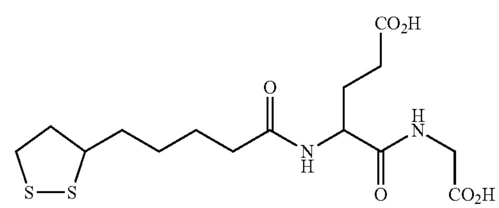 [SMILES: O=C(O)CCC(NC(=O)CCCCC1CCSS1)C(=O)NCC(=O)O] |
| E | (R/S)Lip-DG-OH | 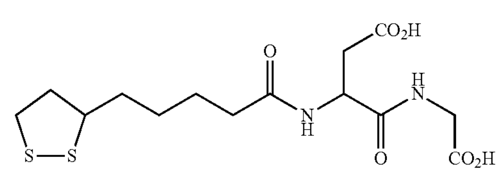 [SMILES: O=C(O)CNC(=O)C(CC(=O)O)NC(=O)CCCCC1CCSS1] |

TABLE A-continued

Chemical Name and Structure of Exemplary Compounds of the Invention

| Entry | Chemical Name | Structure |
|---|---|---|
| F | (R/S)Lip-QG-OH | 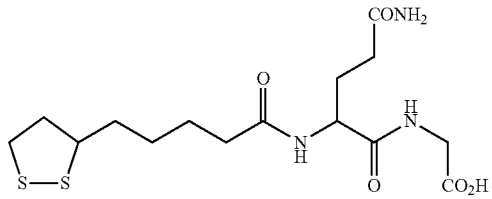 [SMILES: NC(=O)CCC(NC(=O)CCCCC1CCSS1)C(=O)NCC(=O)O] |
| G | RLip-EE-OH | 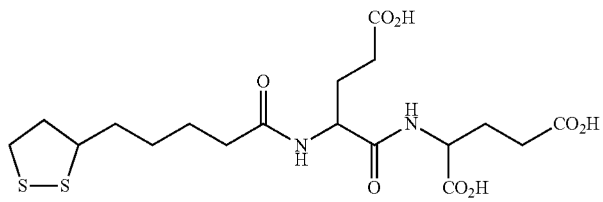 [SMILES: O=C(O)CCC(NC(=O)C(CCC(=O)O)NC(=O)CCCCC1CCSS1)C(=O)O] |
| H | RLip-ES-OH | 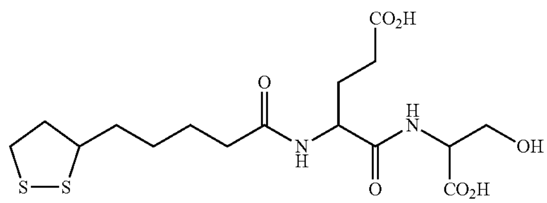 [SMILES: O=C(O)CCC(NC(=O)CCCCC1CCSS1)C(=O)NC(CO)C(=O)O] |
| I | (R/S)Lip-HA-OH | 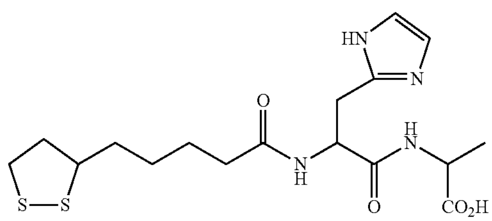 [SMILES: CC(NC(=O)C(Cc1ncc[nH]1)NC(=O)CCCCC1CCSS1)C(=O)O] |
| J | RLip-YA-OH | 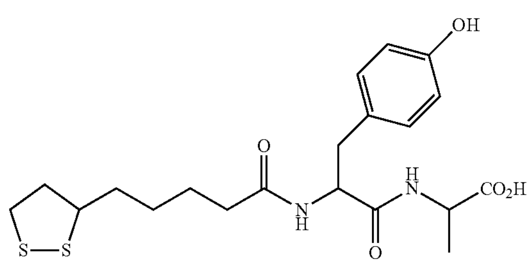 [SMILES: CC(NC(=O)C(Cc1ccc(O)cc1)NC(=O)CCCCC1CCSS1)C(=O)O] |
| K | RLip-AE-OH | 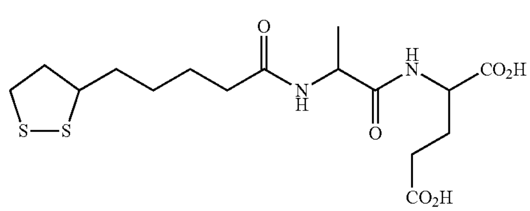 [SMILES: CC(NC(=O)CCCCC1CCSS1)C(=O)NC(CCC(=O)O)C(=O)O] |
| L | RLip-Glu-Sar-OH | 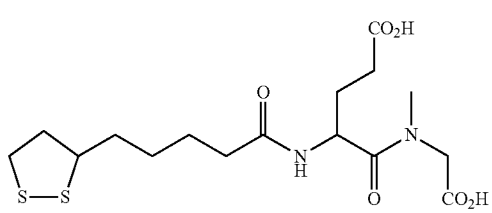 [SMILES: CN(CC(=O)O)C(=O)C(CCC(=O)O)NC(=O)CCCCC1CCSS1] |

TABLE A-continued

Chemical Name and Structure of Exemplary Compounds of the Invention

| Entry | Chemical Name | Structure |
|---|---|---|
| M | RLip-Glu-βAla-OH | 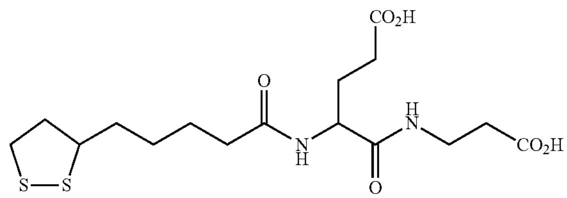 [SMILES: O=C(O)CCNC(=O)C(CCC(=O)O)NC(=O)CCCCC1CCSS1] |
| N | RLip-Glu-Tau-OH | 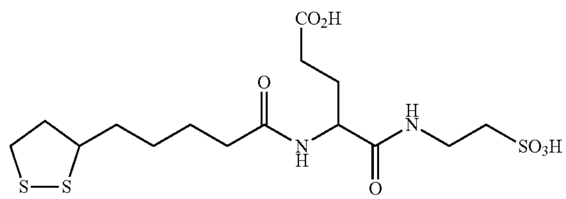 [SMILES: O=C(O)CCC(NC(=O)CCCCC1CCSS1)C(=O)NCCS(=O)(=O)O] |
| O | RLip-DA-OH | 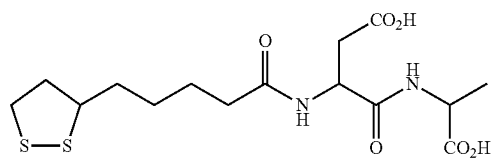 [SMILES: CC(NC(=O)C(CC(=O)O)NC(=O)CCCCC1CCSS1)C(=O)O] |
| P | RLip-EE-NH$_2$ | 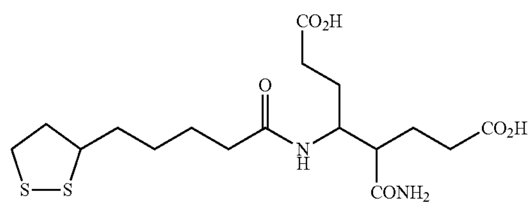 [SMILES: NC(=O)C(CCC(=O)O)C(CCC(=O)O)NC(=O)CCCCC1CCSS1] |
| Q | RLip-Y-OH | 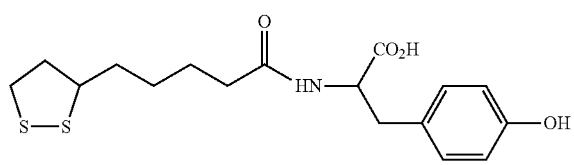 [SMILES: O=C(CCCCC1CCSS1)NC(Cc1ccc(O)cc1)C(=O)O] |
| R | RLip-βAla-OH | 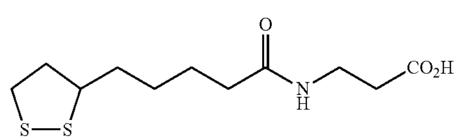 |
| S | N-(RLip)-Aminoadipic-OH<br>RLip-Aad | 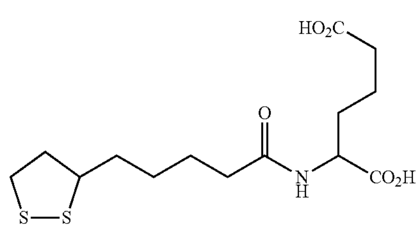 [SMILES: O=C(O)CCCC(NC(=O)CCCCC1CCSS1)C(=O)O] |
| T | RLip-D-OH | 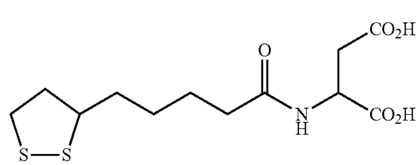 [SMILES: O=C(O)CC(NC(=O)CCCCC1CCSS1)C(=O)O] |

TABLE A-continued
Chemical Name and Structure of Exemplary Compounds of the Invention
| Entry | Chemical Name | Structure |
|---|---|---|
| U | RLip-G-OH | 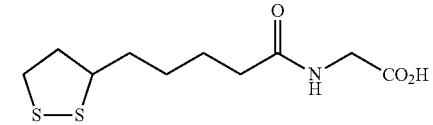 [SMILES: O=C(O)CNC(=O)CCCCC1CCSS1] |
| V | RLip-A-OH | 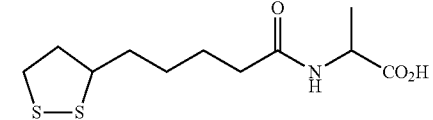 [SMILES: CC(NC(=O)CCCCC1CCSS1)C(=O)O] |
| W | RLip-γ-aminobutyric acid | 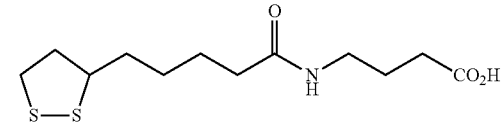 [SMILES: O=C(O)CCCNC(=O)CCCCC1CCSS1] |
| X | RLip-Phospho-Ser-OH<br>RLip-S(O$_3$PH$_2$)—OH | 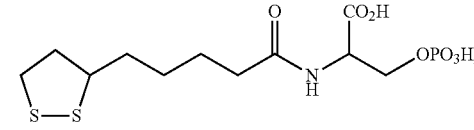 |
| Y | RLip-β-Flouro-Ala-OH | 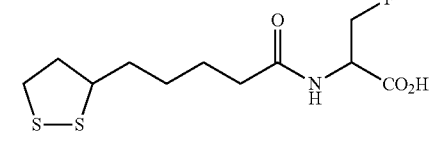 |
| Z | RLip-DGlu-OH<br>RLip-e-OH | 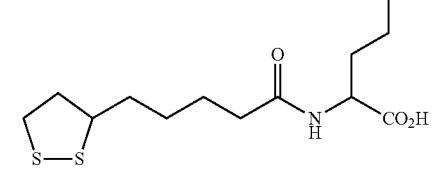 |
| AA | SLip-DGlu-OH<br>SLip-e-OH | 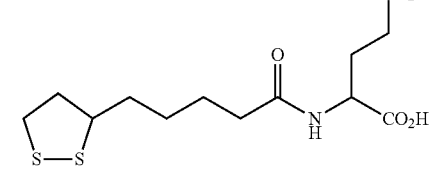 |
| AB | N-(RLip)-4-CarboxyPhe-OH | 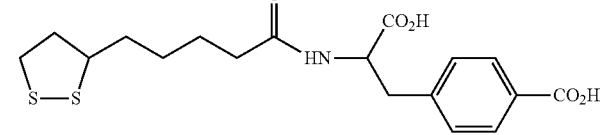 |
| AC | N-(RLip)-3-aminobenzene-sulfonic acid<br>RLip-ABS *Lys | 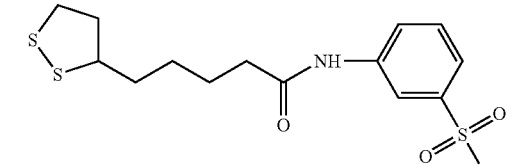 |

TABLE A-continued

Chemical Name and Structure of Exemplary Compounds of the Invention

| Entry | Chemical Name | Structure |
|---|---|---|
| AD | N-(RLip)-Sulfanilic-OH<br>RLip-Sulf | 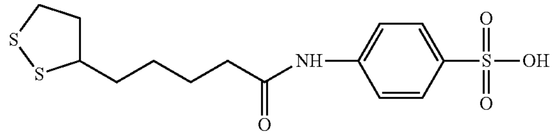 [SMILES: O=C(CCCCC1CCSS1)Nc1ccc(S(=O)(=O)O)cc1] |
| AE | RLip-Cysteic-OH<br>RLip-Cya *2Lys | 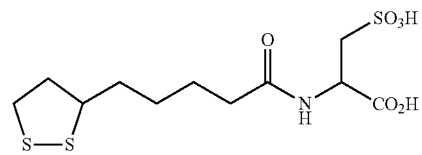 [SMILES: O=C(CCCCC1CCSS1)NC(CS(=O)(=O)O)C(=O)O] |
| AF | N-(RLip)-2-aminoethyl hydrogen sulfate<br>RLip-AEHS *Lys | 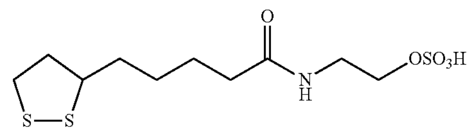 |
| AG | N-(RLip)-O-Phosphoryl-ethanolamine<br>RLip-PEA *2Lys | 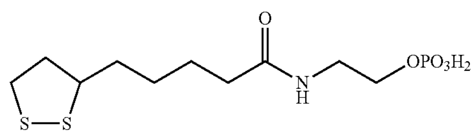 |
| AH | N-(RLip)aminoethyl-phosponic acid<br>RLip-AEP *2Lys | 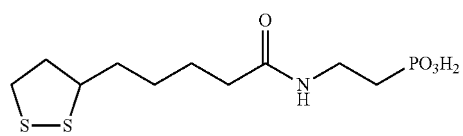 |
| AI | N-(RLip)-4-aminobenzoic acid<br>RLip-PABA | 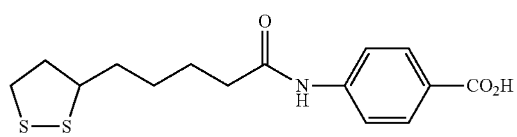 [SMILES: O=C(CCCCC1CCSS1)Nc1ccc(C(=O)O)cc1] |

TABLE B

NMR Data, HPLC Data, and Mass Spectroscopy Data of the Compounds of Table A

| Entry | $^1$H NMR | HPLC Retention Time (min)/Purity (%) | Mass |
|---|---|---|---|
| A | Dithiolane —CH—S— m, 1H, δ 3.12<br>Taurinyl —CH2—<br>m, 2H, δ 3.65, t, 2H, δ 2.98 | 8.29<br>(100) | Calc: 313<br>Found (M − 1): 312 |
| B | Dithiolane —CH—S— m, 1H, δ 3.12<br>Iminodiacetic —CH2— d, 4H, δ 4.20 | 11.4<br>(90) | Calc: 321<br>Found (M − 1): 320 |
| C | Dithiolane —CH—S— m, 1H, δ 3.05<br>Glutamyl αC—H m, 1H, δ 4.37 | 11.7<br>(78) | Calc: 335<br>Found (M − 1): 334 |
| D | Dithiolane —CH—S— m, 1H, δ 3.11<br>Glutamyl αC—H m, 1H, δ 4.5<br>Glycinyl —CH2— d, 2H, δ 3.9 | 8.9<br>(98) | Calc: 392<br>Found (M − 1): 391 |
| E | Dithiolane —CH—S— m, 1H, δ 3.10<br>Glutamyl αC—H m, 1H, δ 4.85<br>Glycinyl —CH2— d, 2H, δ 3.9 | 10.0<br>(100) | Calc: 378<br>Found (M + 1): 379 |
| F | NA | 9.19<br>(99.9) | Calc: 391<br>Found (M − 1): 392 |
| G | Dithiolane —CH—S— m, 1H, δ 3.10<br>Glutamyl, Glutamyl<br>αC—H m, 2H, δ 4.40 | 11.0<br>(97) | Calc: 464<br>Found (M + 1): 463 |
| H | Dithiolane —CH—S— m, 1H, δ 3.10<br>Glutamyl αC—H m, 1H, δ 4.45<br>Serinyl αC—H m, 1H, δ 3.90 | 10.3<br>(86) | Calc: 422<br>Found (M − 1): 421 |

TABLE B-continued

NMR Data, HPLC Data, and Mass Spectroscopy Data of the Compounds of Table A

| Entry | ¹H NMR | HPLC Retention Time (min)/Purity (%) | Mass |
|---|---|---|---|
| I | NA | 9.16/9.29 (99) | Calc: 414<br>Found (M + 1): 415 |
| J | Dithiolane —CH—S— m, 1H, δ 3.10<br>Alaninyl, Tyrosinyl αC—H<br>m, 1H, δ 4.63 m, 1H, δ 4.40 | 13.1 (98) | Calc: 440<br>Found (M − 1): 439 |
| K | NA | 11.25 (98) | Calc: 406<br>Found (M − 1): 405 |
| L | Dithiolane —CH—S— m, 1H, δ 3.10<br>Sarcosine —CH2— m, 2H, δ 4.48 | 11.4 (89) | Calc: 406<br>Found (M − 1): 405 |
| M | Dithiolane —CH—S— m, 1H, δ 3.10<br>Glutamyl αC—H m, 1H, δ 4.40 | 10.9 (100) | Calc: 406<br>Found (M − 1): 405 |
| N | Dithiolane —CH—S— m, 1H, δ 3.18<br>Glutamyl αC—H m, 1H, δ 4.2<br>Taurinyl —CH2—<br>m, 2H, δ 3.36, t, 2H, δ 2.85 | 9.05 (100) | Calc: 442<br>Found (M − 1): 441 |
| O | Dithiolane —CH—S— m, 1H, δ 3.05<br>Aspartyl, Alaninyl αC—H<br>m, 1H, δ 4.70 m, 1H, δ 4.28 | 15.3 (98) | Calc: 392<br>Found (M − 1): 391 |
| P | Dithiolane —CH—S— m, 1H, δ 3.05<br>Glutamyl, Glutamyl<br>αC—H m, 2H, δ 4.25 | 10.8 (100) | Calc: 463<br>Found (M − 1): 462 |
| Q | NA | 12.98 (95) | Calc: 369<br>Found (M + 1): 370 |
| R | NA | 10.95 (100) | Calc: 277<br>Found (M + 1): 278 |
| S | NA | 11.23 (96) | Calc: 349<br>Found (M + 1): 350 |
| T | NA | 10.4 (98) | Calc: 321<br>Found (M + 1): 322 |
| U | NA | 10.7 (100) | Calc: 263<br>Found (M + 1): 264 |
| V | NA | 11.76 (100) | Calc: 277<br>Found (M + 1): 278 |
| W | NA | 11.55 (98) | Calc: 291<br>Found (M + 1): 292 |
| X | NA | 8.19 (96) | Calc: 373<br>Found (M + 1): 374 |
| Y | NA | 12.49 (100) | Calc: 295<br>Found (M + 1): 296 |
| Z | NA | 11.6 (99) | Calc: 335<br>Found (M + 1): 336 |
| AA | NA | 11.6 (97) | Calc: 335<br>Found (M + 1): 336 |
| AB | NA | 12.69 (99) | Calc: 397<br>Found (M + 1): 398 |
| AC | NA | 12.50 (95) | Calc: 361<br>Found (M − 1): 360 |
| AD | NA | 12.37 (92) | Calc: 361<br>Found (M − 1): 360 |
| AE | Dithiolane —CH—S— m, 1H, δ 3.75<br>Lys αC—H m, 1H, δ 3.75<br>Cysteic αC—H m, 1H, δ 4.55 | 7.61 (97) | Calc: 359<br>Found (M + 1): 360 |
| AF | Dithiolane —CH—S— m, 1H, δ 3.65<br>Lys αC—H t, 1H, δ 3.75<br>AEHS —CH2— t, 2H, δ 4.16 | 9.05 (100) | Calc: 329<br>Found (M − 1): 328 |
| AG | Dithiolane —CH—S— m, 1H, δ 3.65<br>Lys αC—H t, 1H, δ 3.75<br>PEA —CH2— q, 2H, δ 3.84 | 8.32 (89) | Calc: 329<br>Found (M − 1): 328 |
| AH | Dithiolane —CH—S— m, 1H, δ 3.25<br>Lys αC—H t, 1H, δ 3.77<br>Aminoethyl —CH2— m, 2H, δ 2.05 | 8.63 (98) | Calc: 313<br>Found (M − 1): 312 |
| AI | NA | 15.25 (99) | Calc: 325<br>Found (M + 1): 326 |

Example 2

Efficacy of Select Lipoyl Compounds of the Invention in a Rat Model of MI/AR Injury Materials and Methods A rat model of MI/AR injury was used as an in vivo screen to determine if the compounds of Tables 1-5 were cardioprotective (e.g., against myocardial ischemia-reperfusion injury). This model is analogous to the ischemia-reperfusion injury observed in cardiac patients following coronary occlusions and cardiac surgery procedures, such as coronary artery bypass grafting (CABG) (Matsui, T., Tao, J., del Monte, F., Lee, K.-H. et al., Akt Activation Preserves Cardiac Function and Prevents Injury After Transient Cardiac Ischemia In vivo, *Circulation* 2001, 104:330, the teachings of which are incorporated herein by reference in their entirety).

General Procedure

The circumflex branch of the left coronary artery (LCA) was ligated temporarily to induce regional ischemia in the left ventricular mass, followed by the injection of fluorescent microspheres to delineate the ischemic region. 15 minutes prior to ligation (pre-occlusion, pre-ischemic episode), a compound from Tables 1-5 was administered to the animals. Doses of the compounds listed in Tables 1-5 ranged from 1-20 mg/kg. The animals were sacrificed about 24 hours after reperfusion and the hearts were excised, sectioned and stained with triphenyltetrazolium. The direct impact of the pharmacologic intervention was determined by measuring the myocardial infarct area (MI), the ischemic area at risk (AR) and the left ventricular area (LV). The reduction of MI over the AR (MI/AR ratio) was used as the primary measure of drug efficacy relative to vehicle controls. The results are reported in Tables 1-5.

TABLE 1

Di-amino Acids Containing an Acidic Functionality

| Entry | Name | Structure | MI/AR Reduction (%) |
|---|---|---|---|
| 1 | N-(R)-lipoyl-L-glutamyl-L-alanine (RLip-EA-OH) | 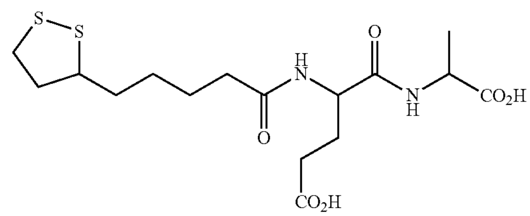 [SMILES: CC(NC(=O)C(CCC(=O)O)NC(=O)CCCCC1CCSS1)C(=O)O] | 31 |
| 2 | N-lipoyl-L-aspartylglycine (RLip-DG-OH) | 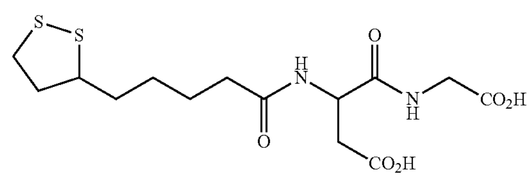 [SMILES: O=C(O)CNC(=O)C(CC(=O)O)NC(=O)CCCCC1CCSS1] | 28 |
| 3 | N-(R)-lipoyl-L-tyrosinyl-L-alanine (RLip-YA-OH) | 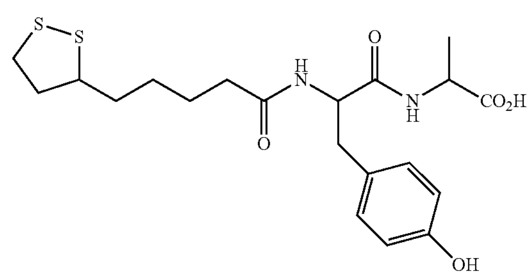 [SMILES: CC(NC(=O)C(Cc1ccc(O)cc1)NC(=O)CCCCC1CCSS1)C(=O)O] | 31 |
| 4 | N-(R)-lipoyl-L-glutamyltaurine (RLip-E-Tau-OH) | 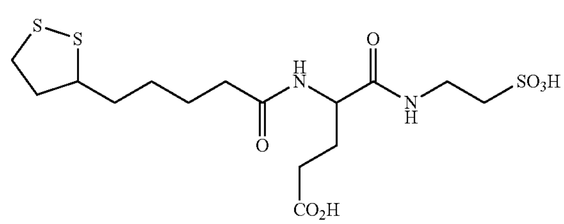 [SMILES: O=C(O)CCC(NC(=O)CCCCC1CCSS1)C(=O)NCCS(=O)(=O)O] | 33 |

TABLE 1-continued

Di-amino Acids Containing an Acidic Functionality

| Entry | Name | Structure | MI/AR Reduction (%) |
|---|---|---|---|
| 5 | N-(R)-lipoyl-L-alanyl-L-glutamic acid (RLip-AE-OH) | 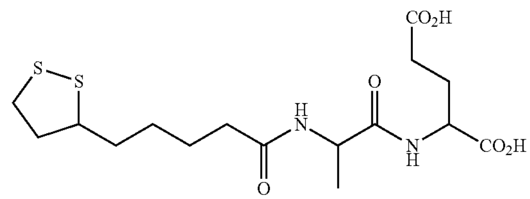 [SMILES: CC(NC(=O)CCCCC1CCSS1)C(=O)NC(CCC(=O)O)C(=O)O] | 24 |

TABLE 2

Single Amino Acid Containing Acidic Functionality

| Entry | Name | Structure | MI/AR Reduction (%) |
|---|---|---|---|
| 6 | N-(R)-lipoyl-L-4-carboxy-phenylalanine (RLip-(4-carboxy)Phe-OH) | 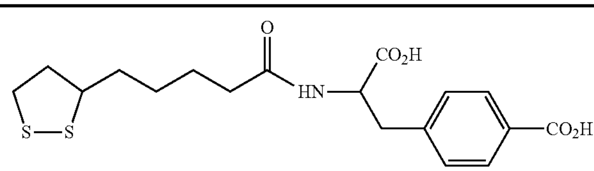 | 26 |
| 7 | N-(R)-lipoyl-fluoroalanine RLip-fluoroalanine | 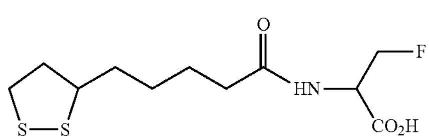 [SMILES: O=C(CCCCC1CCSS1)NC(CF)C(=O)O] | 10 |
| 8 | N-(R)-lipoyl-L-tyrosine (RLip-Y-OH) | 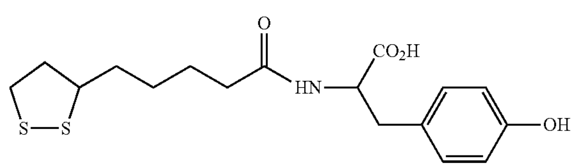 [SMILES: O=C(CCCCC1CCSS1)NC(Cc1ccc(O)cc1)C(=O)O] | 29 |
| 9 | N-(R)-lipoyl-L-glutamic acid (RLip-E-OH) | 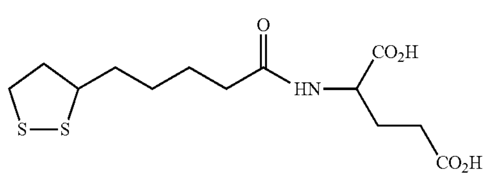 [SMILES: O=C(O)CCC(NC(=O)CCCCC1CCSS1)C(=O)O] | 33 |
| 10 | N-(R)-lipoyl-L-cysteic acid RLip-Cya-OH | 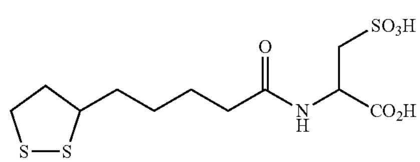 [SMILES: O=C(CCCCC1CCSS1)NC(CS(=O)(=O)O)C(=O)O] | 30 |
| 11 | N-(R)-lipoyliminodiacetic acid RLip-Idaa | 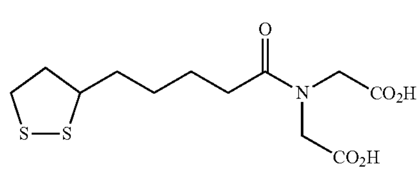 [SMILES: O=C(O)CN(CC(=O)O)C(=O)CCCCC1CCSS1] | 21 |

TABLE 3

Alkyl Acids

| Entry | Name | Structure | MI/AR Reduction (%) |
|---|---|---|---|
| 12 | N-(R)-lipoyl-β-alanine RLip-βAla-OH | 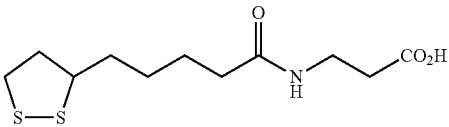 | 39 |
| 13 | N-(R)-lipoyl-taurine RLip-Tau-OH | 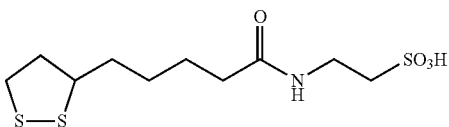 | 45 to 52 |
| 14 | N-(R)-lipoyl-aminoethyl hydrogen-sulfate | 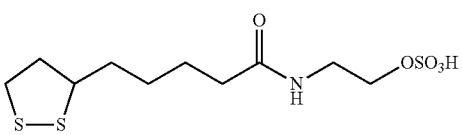 | 30 |
| 15 | N-(R)-lipoyl-aminoethyl-phosphonic acid | 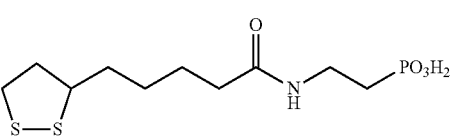 | 53 |
| 16 | N-(R)-lipoyl-aminoethyl dihydrogen-phosphate N-(R)-lipoyl-O-phosphoryl-ethanolamine | 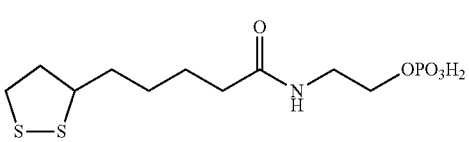 | 47 |

TABLE 4

Alkyl Bis-Acids

| Entry | Name | Structure | MI/AR Reduction (%) |
|---|---|---|---|
| 9 | N-(R)-lipoyl-L-glutamic acid (RLip-E-OH) | 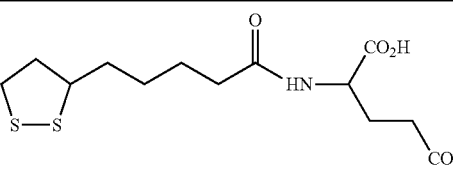 | 33 |
| 10 | N-(R)-lipoyl-L-cysteic acid RLip-Cya-OH | 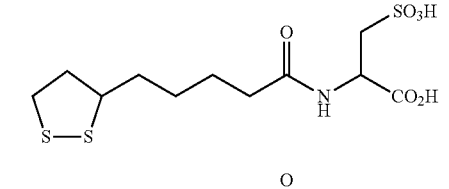 | 30 |
| 11 | N-(R)-lipoylimmodi-acetic acid RLip-Idaa | 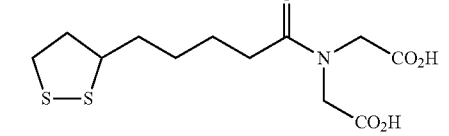 | 21 |

TABLE 5

Aromatic Acids

| Entry | Name | Structure | MI/AR Reduction (%) |
|---|---|---|---|
| 17 | N-(R)-lipoyl-para-aminobenzoic acid (RLip-PABA) | (structure) | 22 |
| 6 | N-(R)-lipoyl-L-4-carboxy-phenylalanine (R)Lip-(4-carboxy) F—OH) | (structure) | 26 |
| 18 | N-(R)-lipoyl-meta-aminobenzene sulfonic acid | (structure) | 33 |
| 19 | N-(R)-lipoyl-para-aminobenzene sulfonic acid N-(R)-lipoyl-sulfanilic acid | (structure) | 44 |
| 8 | N-(R)-lipoyl-L-tyrosine (RLip-Y-OH) | (structure) | 29 |

Detailed Procedure

Male Sprague-Dawley rats between 300 and 350 g were used for these experiments. Anesthesia was induced with 3-4% isoflurane in an induction chamber. After induction, anesthesia was maintained at a surgical plane with 1.5-2.0% isoflurane, administered by a Rodent Ventilator through a 16-gauge angiocatheter introduced orally into the trachea. The ventilator was set at 2.5 cc at a rate of 60-65 breaths per minute to maintain ventilation during surgery. The core temperature of the animal was monitored and maintained at 37° C. using a rectal probe and a heating lamp attached to a temperature controller.

A left anterior thoracotomy was performed and the heart was exposed using a vertical pericardotomy. The circumflex branch of the left coronary artery (LCx) was ligated approximately 4 mm from the aorta using a cardiovascular 7.0 monofilament suture on an 11 mm needle to induce ischemia in the left ventricle.

Fluorescent microspheres (300 μL) were injected into the left ventricular cavity 10-20 minutes after the ligation to delineate the ischemic area. The suture was removed 30 minutes after ligation to reperfuse the ischemic area and the ischemic area was checked for reperfusion.

The chest was then closed in layers using absorbable suture (Dexon 5-0) for the muscle layers and monofilament Nylon 5-0 suture was used to close the cutaneous layer. The animals were allowed to recover, then were returned to the colony.

Twenty-four hours after reperfusion, anesthesia was induced using ketamine hydrochloride and the chest was opened. The animals were sacrificed with 15% potassium chloride aqueous solution (w/v) injected into the LV cavity to arrest the heart in diastole. The heart was excised distal to the aortic valve and washed with saline to remove the blood. Sagittal slices of the heart were obtained between the base of the ventricle and the apex. Five slices of heart tissue were obtained, each 2 mm thick. The slices were immersed in a 1% 2,3,5-triphenyl-2H-tetrazolium chloride (TTC) in saline solution and then stored in the dark for 30 minutes to stain.

Images of the slices were obtained under bright field (to observe the TTC staining) and under fluorescence (to observe the microspheres). The area at risk was determined by the absence of microspheres and the infarct area was determined by the absence of TTC staining Results The compounds of Tables 1-5, administered as an intravenous injection, effectively reduced the myocardial infarct (MI) size relative to the area at risk (AR). A significant reduction in the area of cardiac damage was observed in myocardial tissue sections following treatment with a compound of Tables 1-5.

Example 3

Efficacy of Select Lipoyl Compounds of the Invention in a PAC Rat Model of Ischemia-Induced Renal Injury Materials and Methods A partial aortic clamping (PAC) rat model of ischemia-induced renal injury was used as an in vivo screen to determine if RLip-EA-OH (Entry 1), RLip-Cya-OH (Entry 10), RLip-Tau (Entry 13), and RLip-aminoethylphosphonic acid (Entry 15) were renal-protective (e.g., against renal ischemia-reperfusion injury). This model simulates ischemia-reperfusion injury observed in renal patients following ischemia-induced renal failure (Molitoris, B. A., Dagher, P. C., Sandoval, R. M., Campos, S. B., Ashush, H., Fridman, E., Brafman, A. Faerman, A., Atkinson, S. J., Thompson, J. D., Kalinski, H., Skaliter, R., Erlich, S., Feinstein, E. "siRNA Targeted to p53 Attenuates Ischemic and Cisplatin-Induced Acute Kidney Injury." *J Am Soc Nephrol*, 2009, vol. 20, 1754-1764, the teachings of which are incorporated herein by reference to their entirety). Serum creatinine concentrations (SCr) typically rise due to renal ischemia and effective treatment should show a reduction in serum creatinine concentrations. Reduction in serum creatinine concentrations after renal ischemia induction indicates that the administered compound is has a protective effect and is effective in reducing ischemia-induced kidney injury.

General Procedure

The abdominal aorta just below the renal arteries was isolated and temporarily ligated to induce regional ischemia using an aortic clamp. An initial blood sample was drawn at study initiation for baseline creatinine measurement and at 24 hours post-surgery for functional evaluation of the severity of kidney injury. The animals were sacrificed about 24 hours after reperfusion.

Detailed Procedure

Male Sprague-Dawley rats between 200 to 250 g were used for these experiments. Anesthesia was induced with 5% halothane and maintained with 1-1.5% halothane in oxygen-enriched air via a face mask. The rats were maintained on a warming blanket throughout the procedure to maintain body temperature at 37° C. After shaving the abdomen of the rat, a midline incision was made through the skin and musculature to expose the abdominal cavity to quantify the aortic blood flow (ABF).

The abdominal aorta just below the renal arteries was isolated through blunt dissection from the inferior vena cava, and an ultrasonic probe (2.0-mm diameter, Transit Time Perivascular Flowmeter TS420) was placed and secured. The upper abdominal aorta was then isolated through blunt dissection and freed from the surrounding structures to expose the aorta between the celiac artery and superior mesenteric artery.

Aortic clamps comprised of two 4-mm in length polyethylene tubes (PE-100, 0.86-mm diameter) were then placed around the aorta to induce renal ischemia. One clamp was placed around the aorta and the other was placed to exert variable tension via a 10-in. 3.0 silk suture. The silk thread was then tied and the tension on the two ends of the thread increased until there was a 90% reduction of initial (ABF) rate measured on the ultrasonic probe reader. A 10% baseline blood flow was maintained for a period of 30 minutes.

RLip-EA-OH (Entry 1) at 10 mg/kg; RLip-Cya-OH (Entry 10) at 3 mg/kg; RLip-Tau (Entry 13) at 3 mg/kg; and RLip-aminoethylphosponic acid at 10 mg/kg, 3 mg/kg, and 1 mg/kg were administered intravenously via the femoral vein as a bolus dose 15 minutes prior to ischemia. A 0.15-mL venous blood sample was drawn at study initiation for baseline creatinine measurement and at 24 hours postsurgery for functional evaluation of the severity of kidney injury. Serum creatinine concentrations were then measured on a Creatinine Analyzer 2. The efficacy of RLip-EA-OH and RLip-Tau were measured against the results of vehicle-treated animals in the blinded studies. A 2-tail t-test was used to determine differences between treatments.

Results

RLip-EA-OH (Entry 1), RLip-Cya-OH (Entry 10), RLip-Tau (Entry 13), and RLip-aminoethylphosphonic acid (Entry 15), administered intravenously, effectively reduced serum creatinine concentrations relative to the control animals, as shown in Table 6. This reduction in SCr following treatment indicated that RLip-EA-OH, RLip-Cya-OH, RLip-Tau, and RLip-aminoethylphosphonic acid had protective effects and minimized renal ischemic injury. The data for reduction in cardiac injury reported in the last column in Table 6 were obtained using the procedure described in Example 2.

TABLE 6

Effects of compounds on renal ischemia reperfusion injury in PAC rat model and heart ischemia reperfusion injury in LCA rat model.

| Dose Group | Reduction of SCr vs. control | Reduction in Cardiac injury |
| --- | --- | --- |
| Vehicle (Meta) | — | — |
| Lip-EA 10 mg/kg | 39.5% | 33% |
| Lip-Tau 3 mg/kg | 39.5% | 50% |
| Lip-Cya-OH 3 mg/kg | 39.5% | 30% |
| Lip-aminoethyl phosphonic acid 10 mg/kg | 76.0% | 32% |
| Lip-aminoethyl phosphonic acid 3 mg/kg | 28.6% | 50% |
| Lip-aminoethyl phosphonic acid 1 mg/kg | 28.6% | 30% |

The relevant teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A composition comprising:
   (i) a compound represented by the following structural formula:

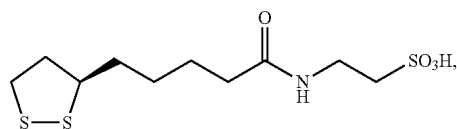 [SMILES: O=C(CCCC[C@@H]1CCSS1)NCCS(=O)(=O)O]

or a pharmaceutically acceptable salt thereof, wherein the enantiomeric excess of the compound or pharmaceutically acceptable salt is at least or about 90%; and
   (ii) a pharmaceutically acceptable carrier or diluent.

2. The composition of claim 1, wherein the enantiomeric excess of the compound or pharmaceutically acceptable salt is at least or about 95%.

3. The composition of claim 2, wherein the enantiomeric excess of the compound or pharmaceutically acceptable salt is at least or about 99%.

4. The composition of claim 1, adapted for oral administration.

5. The composition of claim 4, in the form of a tablet or capsule.

6. The composition of claim 4, in the form of a suspension.

7. The composition of claim 4, in the form of a liquid.

8. A method of inhibiting an ischemia or ischemia-reperfusion injury to a cell, tissue or organ, ex vivo, prior to a therapeutic intervention, comprising contacting the cell, tissue or organ with an effective amount of the composition of claim 1.

9. A method of inhibiting apoptotic cell death in a subject in need thereof, comprising administering to the subject an effective amount of the composition of claim 1.

10. A method of inhibiting apoptotic cell death in a cell, a tissue or an organ, wherein the cell, tissue or organ has experienced an ischemia or other condition or disorder that results in excessive or unwanted cell death, the method comprising the cell, tissue or organ in need thereof with an effective amount of the composition of claim 1.

\* \* \* \* \*